US012303856B2

(12) United States Patent
Zhang et al.

(10) Patent No.: US 12,303,856 B2
(45) Date of Patent: May 20, 2025

(54) HYDROXYETHYL CELLULOSE MICROCAPSULES

(71) Applicant: International Flavors & Fragrances Inc., New York, NY (US)

(72) Inventors: Yi Zhang, Union Beach, NJ (US); Yabin Lei, Union Beach, NJ (US); Li Xu, Union Beach, NJ (US); Ronald Gabbard, Union Beach, NJ (US); Lewis Michael Popplewell, Union Beach, NJ (US); Julie Ann Wieland, Union Beach, NJ (US); Takashi Sasaki, Union Beach, NJ (US)

(73) Assignee: INTERNATIONAL FLAVORS & FRAGRANCES INC., New York, NY (US)

( * ) Notice: Subject to any disclaimer, the term of this patent is extended or adjusted under 35 U.S.C. 154(b) by 641 days.

(21) Appl. No.: 17/416,090

(22) PCT Filed: Dec. 17, 2019

(86) PCT No.: PCT/US2019/066975
§ 371 (c)(1),
(2) Date: Jun. 18, 2021

(87) PCT Pub. No.: WO2020/131956
PCT Pub. Date: Jun. 25, 2020

(65) Prior Publication Data
US 2022/0071864 A1 Mar. 10, 2022

Related U.S. Application Data

(60) Provisional application No. 62/803,024, filed on Feb. 8, 2019.

(51) Int. Cl.
| | | |
|---|---|---|
| *B01J 13/16* | (2006.01) |
| *A61K 8/11* | (2006.01) |
| *A61K 8/34* | (2006.01) |
| *A61K 8/37* | (2006.01) |
| *A61K 8/44* | (2006.01) |
| *A61K 8/73* | (2006.01) |
| *A61K 8/92* | (2006.01) |
| *A61K 9/50* | (2006.01) |
| *A61Q 5/02* | (2006.01) |
| *A61Q 5/12* | (2006.01) |
| *A61Q 13/00* | (2006.01) |
| *A61Q 15/00* | (2006.01) |
| *A61Q 19/00* | (2006.01) |
| *A61Q 19/10* | (2006.01) |
| *B01J 13/20* | (2006.01) |
| *C08G 18/64* | (2006.01) |
| *C08G 18/70* | (2006.01) |
| *C08K 5/07* | (2006.01) |
| *C11D 3/00* | (2006.01) |
| *C11D 3/50* | (2006.01) |

(52) U.S. Cl.
CPC ............ *B01J 13/16* (2013.01); *A61K 8/345* (2013.01); *A61K 8/375* (2013.01); *A61K 8/44* (2013.01); *A61K 8/73* (2013.01); *A61K 8/731* (2013.01); *A61K 8/736* (2013.01); *A61K 8/922* (2013.01); *A61K 9/5047* (2013.01); *A61K 9/5089* (2013.01); *A61Q 5/02* (2013.01); *A61Q 5/12* (2013.01); *A61Q 15/00* (2013.01); *A61Q 19/007* (2013.01); *A61Q 19/10* (2013.01); *B01J 13/206* (2013.01); *C08G 18/6484* (2013.01); *C08G 18/705* (2013.01); *C08K 5/07* (2013.01); *C11D 3/001* (2013.01); *C11D 3/0015* (2013.01); *A61K 8/11* (2013.01); *A61Q 13/00* (2013.01); *C11D 3/505* (2013.01); *C11D 2111/12* (2024.01)

(58) Field of Classification Search
CPC ............ A61K 8/375; A61K 8/44; A61K 8/73; A61K 8/731; A61K 8/736; A61K 8/922; A61K 9/5047; A61K 9/5089; A61K 8/11; A61Q 5/02; A61Q 5/12; A61Q 15/00; A61Q 19/007; A61Q 19/10; A61Q 13/00; B01J 13/206; C08G 18/6484; C08G 18/705; C08K 5/07; C11D 3/001; C11D 3/0015; C11D 2111/12; C11D 3/505
See application file for complete search history.

(56) References Cited

U.S. PATENT DOCUMENTS

| | | | | |
|---|---|---|---|---|
| 4,353,809 | A | * | 10/1982 | Hoshi ................ B01J 13/16 428/914 |
| 8,765,659 | B2 | | 7/2014 | Gizaw et al. |
| 9,011,887 | B2 | | 4/2015 | Chieffi et al. |
| 9,334,469 | B2 | | 5/2016 | Chen et al. |
| 9,725,684 | B2 | | 8/2017 | Fernandes et al. |
| 10,085,925 | B2 | | 10/2018 | Lei et al. |
| 2007/0138672 | A1 | * | 6/2007 | Lee ................... B01J 13/14 264/4.1 |
| 2010/0180386 | A1 | | 7/2010 | Bianchetti et al. |
| 2013/0017239 | A1 | | 1/2013 | Petit et al. |

(Continued)

FOREIGN PATENT DOCUMENTS

| | | |
|---|---|---|
| CN | 101984185 B | 9/2012 |
| EP | 1797946 A2 | 6/2007 |

OTHER PUBLICATIONS

International Preliminary Report on Patentability in PCT/US2019/066975, dated Jun. 16, 2021.
International Search Report and Written Opinion in PCT/US2019/066975, dated Apr. 16, 2020.
Office Communication dated Feb. 26, 2021 in U.S. Appl. No. 16/086,198, filed Sep. 18, 2018.

*Primary Examiner* — Doan T Phan

(57) ABSTRACT

Disclosed are microcapsules each having a microcapsule core and a microcapsule wall encapsulating the microcapsule core. The microcapsule core contains an active material and the microcapsule wall contains hydroxyethyl cellulose moieties. Also disclosed are preparation method and consumer products containing the microcapsules.

16 Claims, No Drawings

(56) References Cited

U.S. PATENT DOCUMENTS

| | | |
|---|---|---|
| 2013/0216596 A1 | 3/2013 | Petit et al. |
| 2014/0322283 A1* | 10/2014 | Berthier ................ C11D 3/505 |
| | | 514/556 |
| 2016/0158121 A1 | 6/2016 | Lei et al. |
| 2017/0216166 A1* | 8/2017 | Sasaki ................ A61K 8/8129 |
| 2018/0078468 A1 | 3/2018 | Jerri et al. |
| 2018/0085291 A1 | 3/2018 | Sasaki et al. |
| 2018/0346648 A1 | 12/2018 | Popplewell et al. |
| 2018/0353399 A1 | 12/2018 | Lei et al. |
| 2020/0306197 A1 | 10/2020 | Brahms et al. |

* cited by examiner

HYDROXYETHYL CELLULOSE MICROCAPSULES

CROSS-REFERENCE TO RELATED APPLICATIONS

This application is a 371 of International Application No. PCT/US2019/066975 filed Dec. 17, 2019 and claims priority to US Application Ser. No. 62/803,024 filed Feb. 8, 2019. The content of all applications are incorporated herein by reference in their entirety.

BACKGROUND

Consumers prefer environment friendly products over synthetic polymers. Conventional delivery systems are widely used in consumer products for releasing a fragrance or flavor to a target area in a controlled manner. The delivery systems are particularly useful for fragrance delivery, which typically utilizes microcapsules formed of synthetic polymers such as melamine formaldehyde, polyurea, or polyacrylate.

Microcapsules prepared from natural materials have been reported in Mint et al., WO2016185171, with a fungal chitosan. However, Mint et al. does not include fragrance performance results. Silk fibroin particles have also been used to encapsulate fragrance oil. See Kaplan et al., US20150164117A1. No performance benefit has been reported in consumer products. U.S. Pat. No. 4,946,624A describes gelatin microcapsules, which only has a modest fragrance performance. These gelatin microcapsules are not good enough for consumer products such as fabric softeners.

Hydroxyethyl cellulose (HEC) is a gelling and thickening agent derived from cellulose. It is widely used in cosmetic, personal care industry, and pharmaceutical products. HEC has also used in microcapsules as an emulsifier, modifier, etc. See e.g., U.S. Pat. No. 8,765,659 B2, U.S. Pat. No. 9,725,684 B2, CN101984185B, US20130017239A1, and US20100180386A1. HEC has been cationically modified and applied as a coating to microcapsules. See, e.g., U.S. Pat. No. 9,011,887 B2, US20180078468, and US20130216596A1. It is reported that HEC is not a preferred surface modifier for microcapsules. See U.S. Pat. No. 9,334,469.

There is a need to develop environment friendly microcapsules with a high fragrance performance for use in laundry, washing, cleaning, surface care and personal and skin care.

SUMMARY OF THE INVENTION

This invention is based on the discovery that certain capsule compositions possess unexpected desirable properties such as high perceived olfactory intensity, great stability, and being friendly to the environment.

Accordingly, one aspect of this invention relates to a microcapsule having a microcapsule core and a microcapsule wall encapsulating the microcapsule core, wherein the microcapsule core contains an active material and the microcapsule wall contains, by weight of the microcapsule wall, 30% to 95% of a first moiety derived from hydroxyethyl cellulose, and 5% to 70% of one or more additional moieties derived from a polyisocyanate, a multi-functional aldehyde, a polyphenol, or any combination thereof.

Preferably, the microcapsule wall contains by weight 35% to 90% (e.g., 40% to 80% and 40% to 60%) of the first moiety derived from the hydroxyethyl cellulose, 2% to 30% (e.g., 3% to 20% and 5% to 15%) of a second moiety derived from the polyisocyanate, 1% to 50% (e.g., 2% to 40% and 5% to 30%) of a third moiety derived from the polyphenol (e.g., tannic acid), and optionally 0.5% to 20% (e.g., 1% to 15% and 2% to 10%) of a fourth moiety derived from the multi-functional aldehyde, provided that the total amount of the first, second, third, and fourth moieties is equal to or less than 100%.

Exemplary polyisocyanates includes a trimer of hexamethylene diisocyanate, a trimer of isophorone diisocyanate, a biuret of hexamethylene diisocyanate, a polyisocyanurate of toluene diisocyanate, a trimethylol propane-adduct of toluene diisocyanate, a trimethylol propane-adduct of xylylene diisocyanate, and combinations thereof. Useful multi-functional aldehydes are those having two or more formyl (—CHO) groups such as glutaraldehyde, glyoxal, di-aldehyde starch, malondialdehyde, and combinations thereof.

In some embodiments, the microcapsule shell further comprises a hydroxypropyl cellulose at a level of 1% to 60%.

Preferably, the microcapsule shell constitutes 10% to 90% by weight of the microcapsule, and the microcapsule core constitutes 90% to 10% by weight of the microcapsule. Typically, the microcapsule is a core-shell microcapsule having a size of 0.2 µm to 100 µm in diameter. The core-shell microcapsule has a microcapsule wall surrounding a single shell.

In any of the microcapsules above, the active material is preferably selected from the group consisting of a pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, nanometer to micron size inorganic solid, polymeric or elastomeric particle, taste modulator, cell, probiotic, and combinations thereof. In one embodiment, the active material is a high-performing fragrance.

Optionally, any of the above microcapsules are coated with a deposition polymer selected from the group consisting of trimonium, methacrylamidopropyl trimethyl ammonium, acrylamidopropyl trimethylammonium, acrylamide, acrylic acid, dimethyl ammonium, xlylose, galactose, hydroxypropylated glucose, hydroxyethylated glucose, hydroxymethylated glucose, chitosan, vinylamine, ethylenimine, vinylformamide, vinylpyrrolidone, caprolactone, catechol, vinylalcohol, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, a copolymer of vinylamine and vinylformamide, a copolymer of acrylamide and 3-methacryloylaminopropyl trimethylammonium, a 3-acrylamidopropyl trimethylammonium polymer or its copolymer, a diallyldimethylammoniumchloride polymer and its copolymer, a polysaccharide with saccharide unit functionalized with hydroxypropyl trimonium, and combinations thereof.

Another aspect of this invention relates to a process of preparing a microcapsule composition comprising the steps of: (i) providing an oil-in-water emulsion having a plurality of oil droplets dispersed in an aqueous phase, in which the oil-in-water emulsion contains a surfactant and a polyisocyanate, the oil phase contains an active material, and the aqueous phase contains a hydroxyethyl cellulose (HEC), (ii) obtaining a reaction mixture containing the oil-in-water emulsion, a multi-functional aldehyde and a polyphenol, and (iii) providing a condition sufficient to induce interfacial polymerization in the reaction mixture to form a microcapsule having a microcapsule wall encapsulating a microcapsule core, thereby obtaining the microcapsule composition. The process optionally comprises the step of (iv) curing the microcapsule at 15° C. to 135° C.

The process can also have the step of adding a catalyst (e.g., 1,4-diazabicyclo[2.2.2]octane to the oil-in-water emulsion.

In some embodiments, the condition sufficient to induce crosslinking reaction is heating the reaction mixture to at least 35° C.

Preferably, each oil droplet has a size of 0.1 μm to 100 μm in diameter and each microcapsule has a size of 0.2 μm to 100 μm in diameter.

Suitable surfactants include a polyvinyl alcohol, polystyrene sulfonate, carboxymethyl cellulose, naphthalene sulfonate, polyvinylpyrrolidone, copolymer of vinyl pyrrolidone and quaternized dimethylaminoethyl methacrylate, an octenyl succinic anhydride (OSA) modified starch, OSA modified gum acacia, gum acacia, alginate, carboxylmethylcellulose (CMC), carageenan, xanthan gum, gellan gum, lecithin, modified lecithin, protein, modified protein, pectin, modified pectin, lignin, modified lignin, and combinations thereof.

The polyisocyanate can present either in the oil droplets or the aqueous phase at a level of 0.01% to 10% by weight of the microcapsule composition. The multi-functional aldehyde is typically added. e.g., as an aqueous solution, to the oil-in-water emulsion at a level of 0.1% to 2% by weight of the microcapsule composition and is selected from the group consisting of glutaraldehyde, glyoxal, di-aldehyde starch, malondialdehyde, and combinations thereof. HEC can be added, e.g., as an aqueous solution, to the oil-in-water emulsion a level of 1% to 8% by weight of the microcapsule composition. The multi-functional aldehyde or HEC can be added to the emulsion in two separate solutions or in a single aqueous solution. A polyphenol (e.g., tannic acid) can also be added to the oil-in-water emulsion at a level of 0.5% to 5% by weight of the microcapsule composition.

In some embodiments, hydroxypropyl cellulose is also added to the oil-in-water emulsion at a level of 0.2% to 5% by weight of the microcapsule composition.

Also within the scope of this invention is a microcapsule composition prepared by any methods described above.

Still with the scope of this invention is a microcapsule composition containing a plurality of a microcapsule described above, either dispersed in an aqueous phase as a slurry, or in a dry form such as spray dried particles.

The microcapsule and its composition described above are useful to impart fragrance in consumer products such as a baby care product, a diaper rash cream or balm, a baby powder, a diaper, a bib, a baby wipe, a cosmetic preparation, a powder foundation, a liquid foundation, an eye shadow, a lipstick or lip balm, a home care product, an all-purpose cleaner, a scent drop product, a bathroom cleaner, a floor cleaner, a window cleaner, a plastics polish, a bleach, a toilet cleaner, a toilet rimblock, a bath tissue, a paper towel, a disposable wipe, liquid air freshener, air freshener spray, a spray dispenser product, an incense stick, a rug deodorizer, a candle, a room deodorizer, a liquid dish detergent, an automatic dish detergent, a powder dish detergent, a leather detergent, a tablet dish detergent, a paste dish detergent, a unit dose tablet or capsule, a flavor, a beverage flavor, a diary flavor, a fruit flavor, a miscellaneous flavor, a sweet goods flavor, a tobacco flavor, a toothpaste flavor, a chewing gum, a breath freshener, an orally dissolvable strips, a chewable candy, a hard candy, an oral care product, a tooth paste, a toothbrush, a dental floss, an oral rinse, an tooth whitener, a denture adhesive, a health care device, a tampon, a feminine napkin, an anti-inflammatory balm, an anti-inflammatory ointment, an anti-inflammatory spray, a disinfectant, a personal care product, a soap, a bar soap, a liquid soap, a bath fragrance, a body wash, a non-aerosol body spray, a body milk, a cleanser, a body cream, a hand sanitizer, a hand wash, a functional product base, a sunscreen lotion, a sunscreen spray, a deodorant, an anti-perspirant, an roll-on product, an aerosol product, a natural spray product, a wax-based deodorant, a glycol type deodorant, a soap type deodorant, a facial lotion, a body lotion, a hand lotion, a miscellaneous lotion, a body powder, a shave cream, a shave gel, a shave butter, a bath soak, a shower gel, an exfoliating scrub, a foot cream, a facial tissue, a cleansing wipe, a talc product, a hair care product, a hair care with ammonia, a shampoo, a hair conditioner, a hair rinse, a hair refresher, a hair fixative or styling aid, a hair bleach, a hair dye or colorant, a fabric care product, a fabric softener, a liquid fabric softener, a fabric softener sheet, a drier sheet, a fabric refresher, an ironing water, a detergent, a laundry detergent, a liquid laundry detergent, a powder laundry detergent, a tablet laundry detergent, a laundry detergent bar, a laundry detergent cream, a hand wash laundry detergent, a scent booster, a fragrance, a cologne, compounds, an encapsulated fragrance, a fine fragrance, a men's fine fragrance, a women's fine fragrance, a perfume, a solid perfume, an Eau De Toilette product, a natural spray product, a perfume spray product, an insect repellent product, and a wildlife scent.

The details of one or more embodiments of the invention are set forth in the description below. Other features, objects, and advantages of the invention will be apparent from the description and the claims.

DETAILED DESCRIPTION OF THE INVENTION

It has been found that certain HEC microcapsules have unexpectedly high fragrance performance and are environment friendly. These HEC microcapsule compositions have been successfully incorporated into many consumer applications.

The microcapsule of this invention can be prepared following the steps of: (i) providing an oil-in-water emulsion having a plurality of oil droplets dispersed in an aqueous phase, in which the oil-in-water emulsion contains a polyisocyanate, the oil phase contains an active material, the aqueous phase contains a hydroxyethyl cellulose (HEC), and the oil-in-water emulsion further contains a multi-functional aldehyde, a polyphenol, or both, (ii) providing a condition sufficient to induce interfacial polymerization in the reaction mixture to form a microcapsule having a microcapsule wall encapsulating a microcapsule core, and (iii), optionally, curing the microcapsule at a temperature of 15° C. to 135° C. for 5 minutes to 48 hours. In some embodiments, a catalyst (e.g., 1,4-diazabicyclo[2.2.2]octane is added during step (i) or (ii) to facilitate the polymerization.

The oil-in-water emulsion can be prepared using conventional emulsion techniques by emulsifying an oil phase into an aqueous phase in the presence of a capsule formation aid. In one embodiment, the oil phase contains the active material (such as a fragrance), polyisocyanate and a core solvent (such as caprylic/capric triglyceride). The aqueous phase contains water and HEC with or without a surfactant. In another embodiment, the oil phase contains the active material and a core solvent. The aqueous phase contains water, polyisocyanate, and a capsule formation aid. In still another embodiment, the polyisocyanate is not added in either the oil or aqueous phase before emulsion. It is added to a pre-formed oil-in-water emulsion.

The microcapsule of this invention can also be prepared by printing a microcapsule shell and a microcapsule core using a printing system such as a 3D printer. See WO2016172699A1. The printing steps generally include depositing the active materials and the microcapsule shell material in a layer-by-layer fashion, preferably through separate printer heads. The microcapsule shell material can be polymeric or monomeric materials or oil-in-water emulsions as described herein.

The microcapsules thus prepared each have a particle size (in diameter) in the range from 0.1 microns to 1000 microns (e.g., 0.5 microns to 500 microns, 1 micron to 200 microns, and 1 micron to 100 microns) with a lower limit of 0.1 microns, 0.5 microns, 1 micron, 2 microns, or 5 microns and an upper limit of 1000 microns, 500 microns, 200 microns, 100 microns, 75 microns, 50 microns, or 30 microns.

The microcapsules can be positively or negatively charged with a zeta potential in the range of −200 mV to +200 mV (e.g., 10 mV or greater, 25 mV or greater, 40 mV or greater, 25 mV to 200 mV, and 40 mV to 100 mV) with a lower limit of −200 mV, −150 mV, −100 mV, −50 mV, −25 mV, −10 mV, 0 mV, 10 mV, 20 mV, or 40 mV and an upper limit of 200 mV, 150 mV, 100 mV, 50 mV, 40 mV, 20 mV, 10 mV, 0 mV, −10 mV, and −25 mV. Preferably, the microcapsules each are positively charged. Not to be bound by theory, the positively charged microcapsules have a strong affinity to specific animate and inanimate surfaces (e.g., hair and fabric), and also are unexpectedly stable in certain consumer product bases such as hair conditioners, shampoos, shower gels, and fabric conditioners.

The HEC microcapsules of this invention each have a microcapsule core and a microcapsule wall encapsulating the microcapsule core.

The microcapsule wall is formed of a polymeric network containing one or more encapsulating polymers. Not to be bonded by any theory, two or more encapsulating polymers can be crosslinked or interweaved to form the polymeric network. An exemplary encapsulating polymer is a polyurethane polymer that is the reaction product between HEC and polyisocyanate, in which the hydroxy group (—OH) on HEC reacts with the isocyanate group (—NCO) on the polyisocyanate to form the polyurethane bond. The polyphenol (e.g., tannic acid) also reacts with polyisocyanate to form a polyurethane polymer. Another example of the encapsulating polymer is an acetal or hemi-acetal product between HEC and the multi-functional aldehyde, in which the hydroxy group (—OH) on HEC reacts with the formyl group (—CHO) on the multi-functional aldehyde to form an acetal or hemi-acetal polymer. Polyphenol can also react with the multi-functional aldehyde to form an acetal or hemi-acetal polymer. It is preferred to have both the polyurethane polymer and the acetal/hemi-acetal polymer to form a microcapsule wall with sufficient stability, good degradability, and satisfactory fragrance release profile.

In one example, the microcapsule of this invention have a microcapsule wall formed of a polymeric network containing at least four moieties: the first moiety derived from HEC, the second moiety derived from the polyisocyanate, the third moiety derived from the polyphenol, and the fourth moiety derived from the multi-functional aldehyde.

The microcapsule wall has an inner surface and outer surface. The inner surface is in contact with the microcapsule core. The outer surface is in contact with the environment where the microcapsule resides, e.g., a water phase, skin, and hair.

Hydroxyethyl Cellulose

Hydroxyethyl cellulose (HEC) has been broadly used as a gelling agent, thickening agent, binder, bond strengthener, cement extender, coating and optical brightener aid, coating polymer, filtration control additive, green strength enhancer, protective colloid, rebound or slumping reducer, rheology controller and modifier, lubricity and workability enhancer, suspension and stabilization agent, shape retention enhancer and thickener.

HEC is a nonionic, water-soluble polymer, and typically has a molar mass of 1000 Daltons to 10,000,000 Daltons. Commercial HEC products are sold as a white, free-flowing granular powder. It is available under the trade names of Natrosol™ (Ashland, Covington, Kentucky), CELLO-SIZE™ (Dow, Midland, Michigan), and Tylose™ (ShinEtsu, Tokyo, Japan)

HEC is usually made by reacting ethylene oxide with alkali-cellulose under rigidly controlled conditions, in which ethylene oxide reacts with a hydroxy group on cellulose to form a hydroxyethyl substitution on an anhydroglucose unit of the cellulose. An idealized HEC structure is shown below, with one hydroxyethyl group substitution on the anhydroglucose unit at right and two hydroxyethyl groups on the unit at left:

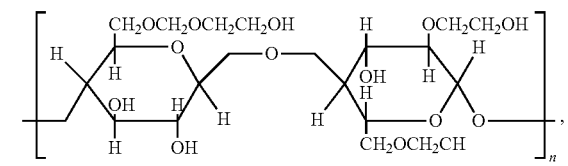

in which n is typically 200 to 4,000.

The manner in which hydroxyethyl groups are added to the anhydroglucose units can be described by degree of substitution (D.S.) and molar substitution (M.S.).

The degree of substitution refers to the average number of hydroxy groups on each anhydroglucose unit that have been reacted with ethylene oxide. Suitable HEC for use in this invention has a DS of 0.1 to 3 (e.g., 0.5 to 3, 1 to 3, 0.5 to 1.5, 0.1, 0.5, 1, 1.5, 2, and 3).

The molar substitution refers to the average number of ethylene oxide added to each anhydroglucose unit. HEC can have an MS of 0.1 to 5 (e.g., 0.5 to 4, 1 to 3, 1.5, and 2).

Typically, HEC constitutes 10% to 95% (e.g., 15% to 90%, 20% to 85%, 25% to 80%, 30% to 75%, 45%, 55%, 65%, and 75%) by weight of the microcapsule wall. In the microcapsule composition, HEC is present at a level of 0.5% to 15% (1% to 10%, 2% to 8%, and 3% to 7%) by weight of the microcapsule composition.

When HEC is used in combination of other polysaccharides or sugar alcohols, the content of HEC can be at the low end of the range, e.g., 10% to 50% and 15% to 40%. When used in combination with hydroxypropyl cellulose (HPC), the ratio between HEC and HPC can be 1:9 to 9:1 (e.g., 2:8 to 8:2, 3:7 to 7:3, 4:6 to 6:4, 1:2, 1:3, 4:1, and 5:1).

Polyisocyanates

Polyisocyanate has at least two isocyanate (—NCO) groups reactive towards HEC or polyphenols. The polyisocyanate can be aromatic, aliphatic, linear, branched, or cyclic. It can be water soluble or water dispersible. Alternatively, it is soluble in an organic solvent or fragrance oil. In some embodiments, the polyisocyanate contains, on average, 2 to 4 isocyanate groups. In particular embodiments, the polyisocyanate contains at least three isocyanate functional groups. In certain embodiments, the polyisocyanate is water insoluble.

In particular embodiments, the polyisocyanate used in this invention is an aromatic polyisocyanate. Desirably, the aromatic polyisocyanate includes a phenyl, tolyl, xylyl, naphthyl or diphenyl moiety as the aromatic component. In certain embodiments, the aromatic polyisocyanate is a polyisocyanurate of toluene diisocyanate, a trimethylol propane-adduct of toluene diisocyanate or a trimethylol propane-adduct of xylylene diisocyanate.

One class of suitable aromatic polyisocyanates are those having the generic structure shown below, and its structural isomers

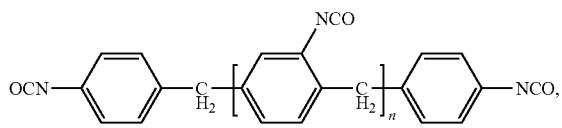

wherein n can vary from zero to a desired number (e.g., 0-50, 0-20, 0-10, and 0-6) depending on the type of cross-linker used. Preferably, the number of n is limited to less than 6. The starting polyisocyanate may also be a mixture of polyisocyanates where the value of n can vary from 0 to 6. In the case where the starting polyisocyanate is a mixture of various polyisocyanates, the average value of n preferably falls in between 0.5 and 1.5. Commercially-available polyisocyanates include products under the trade names of LUPRANATE® M20 (chemical name: polymeric methylene diphenyl diisocyanate, i.e., "PMDI", commercially available from BASF containing isocyanate group "NCO" 31.5 wt %), where the average n is 0.7; PAPI™ 27 (PMDI commercially available from Dow Chemical having an average molecular weight of 340 and containing NCO 31.4 wt %) where the average n is 0.7; MONDUR® MR (PMDI containing NCO at 31 wt % or greater, commercially available from Covestro, Pittsburgh, Pennsylvania) where the average n is 0.8; MONDUR® MR Light (PMDI containing NCO 31.8 wt %, commercially available from Covestro) where the average n is 0.8; MONDUR® 489 (PMDI commercially available from Covestro containing NCO 30-31.4 wt %) where the average n is 1; poly[(phenylisocyanate)-co-formaldehyde] (Aldrich Chemical, Milwaukee, WI), other isocyanate monomers such as DESMODUR® N3200 (poly(hexamethylene diisocyanate) commercially available from Covestro), and Takenate™ D-110N (trimethylol propane-adduct of xylylene diisocyanate, Mitsui Chemicals America, Inc., Rye Brook, NY, containing NCO 11.5 wt %), DESMODUR® L75 (a polyisocyanate base on toluene diisocyanate commercially available from Covestro), and DESMODUR® IL (another polyisocyanate based on toluene diisocyanate commercially available from Covestro).

The structures of certain commercially available polyisocyanates of the invention are shown below:

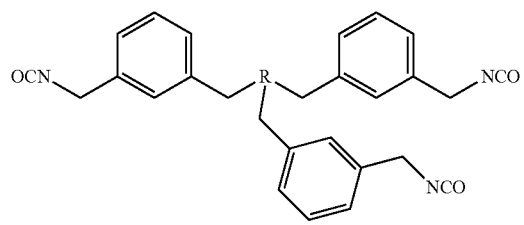

or its structural isomer. R can be a $C_1$-$C_{10}$ alkyl, $C_1$-$C_{10}$ ester, or an isocyanurate. Representative polyisocyanates of this structure are TAKENATE™ D-110N (Mitsui), DESMODUR® L75 (Covestro), and DESMODUR® IL (Covestro).

Polyisocyanate Takenate™ D-110N and other polyisocyanates are commercially available, typically in an ethyl acetate solution. Preferably, ethyl acetate is replaced with a solvent having a high flash point (e.g., at least 100° C., at least 120° C., and at least 150° C.). Suitable solvents include triacetin, triethyl citrate, ethylene glycol diacetate, benzyl benzoate, and combinations thereof.

As an illustration, a trimethylol propane-adduct of xylylene diisocyanate solution in ethyl acetate (Takenate™ D-110N) is combined with benzyl benzoate and vacuum distilled to remove ethyl acetate to obtain a polyisocyanate solution containing about 59% of the trimethylol propane-adduct of xylylene diisocyanate solution and 41% of benzyl benzoate. This polyisocyanate solution has a flash point of at least 60° C. This polyisocyanate solution in benzyl benzoate, together with PVP/PQ-11 or Flexan® II/CMC, can be used to prepare the microcapsule composition of this invention.

Other examples of the aromatic polyisocyanate include 1,5-naphthylene diisocyanate, 4,4'-diphenylmethane diisocyanate (MDI), hydrogenated MDI, xylylene diisocyanate (XDI), tetramethylxylol diisocyanate, 4,4'-diphenyldimethylmethane diisocyanate, di- and tetraalkyl-diphenylmethane diisocyanate, 4,4'-dibenzyl diisocyanate, 1,3-phenylene diisocyanate, 1,4-phenylene diisocyanate, the isomers of tolylene diisocyanate (TDI), 4,4'-diisocyanatophenyl-perfluoroethane, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate, and combinations thereof.

In other particular embodiments, the polyisocyanate is an aliphatic polyisocyanate such as a trimer of hexamethylene diisocyanate, a trimer of isophorone diisocyanate, and a biuret of hexamethylene diisocyanate. Exemplary aliphatic polyisocyanates include commercial products, e.g., BAYHYDUR® N302, BAYHYDUR® N303, BAYHYDUR® N304, and BAYHYDUR® N305, which are aliphatic water-dispersible based on hexamethylene diisocyanate: DESMODUR® N3600, DESMODUR® N3700, and DESMODUR® N3900, which are low viscosity, polyfunctional aliphatic polyisocyanates based on hexamethylene diisocyanate; and DESMODUR® 3600 and DESMODUR® N100 which are aliphatic polyisocyanates based on hexamethylene diisocyanate, each of which is available from Covestro, Pittsburgh, PA). More examples include 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-tri-methylcyclohexane, chlorinated and brominated diisocyanates, phosphorus-containing diisocyanates, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, and combinations thereof. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane, dimer fatty acid diisocyanate, and combinations thereof.

The weight average molecular weight of useful polyisocyanates varies from 200 Da to 2500 Da, 250 Da to 1000 Da and preferable from 275 Da to 500 Da.

The range of the polyisocyanate content can vary from 0.2% to 40% (e.g., 0.4% to 35%, 0.5% to 30%, 1% to 25%, 2% to 25%, and 5% to 20%) by weight of the microcapsule. In a microcapsule composition, the amount of the polyisocyanate varies from 0.1% to 20% (e.g., 0.1% to 15%, 0.2% to 10%, 1.5% to 3.5%, 0.4% to 1.2%, 0.5% to 1%, 0.6%, and 0.8%, all based on the total capsule composition).

The ratio of HEC and polyisocyanate varies from 1:1 to 10:1 (e.g., 2:1 to 9:1, 3:1 to 8:1, 4:1 to 7:1, and 5:1 to 6:1).

During the process of preparing the microcapsule composition of this invention, polyisocyanate can be added to the aqueous phase or to the oil phase. Preferably, polyisocyanate is added to the aqueous phase.

In some embodiments, the polyfunctional isocyanate used in the preparation of the microcapsules of this invention is a single polyisocyanate. In other embodiments the polyisocyanate is a mixture of polyisocyanates. In some embodiments, the mixture of polyisocyanates includes an aliphatic polyisocyanate and an aromatic polyisocyanate. In particular embodiments, the mixture of polyisocyanates is a biuret of hexamethylene diisocyanate and a trimethylol propane-adduct of xylylene diisocyanate. In certain embodiments, the polyisocyanate is an aliphatic isocyanate or a mixture of aliphatic isocyanate, free of any aromatic isocyanate. In other words, in these embodiments, no aromatic isocyanate is used to prepare the encapsulating polymers as capsule wall materials. More polyisocyanate examples can be found in WO 2004/054362 and WO 2017/192648.

Multi-Functional Aldehydes

Multi-functional aldehydes each have two or more formyl groups (—CHO). Suitable multi-functional aldehydes include glutaraldehyde, glyoxal, di-aldehyde starch, malondialdehyde, succinic dialdehyde, 1,3-propane dialdehyde, 1,4-butane dialdehyde, 1,5-pentane dialdehyde, and 1,6-hexane; as well as compounds such as glyoxyl trimer and paraformaldehyde, bis(dimethyl) acetal, bis(diethyl) acetal, polymeric dialdehydes, such as oxidized starch.

Polyphenols

Exemplary polyphenols include those having a 3,4,5-trihydroxyphenyl group or 3,4-dihydroxypheny group. A preferred polyphenol is tannic acid, which has a typical chemical structure as follows:

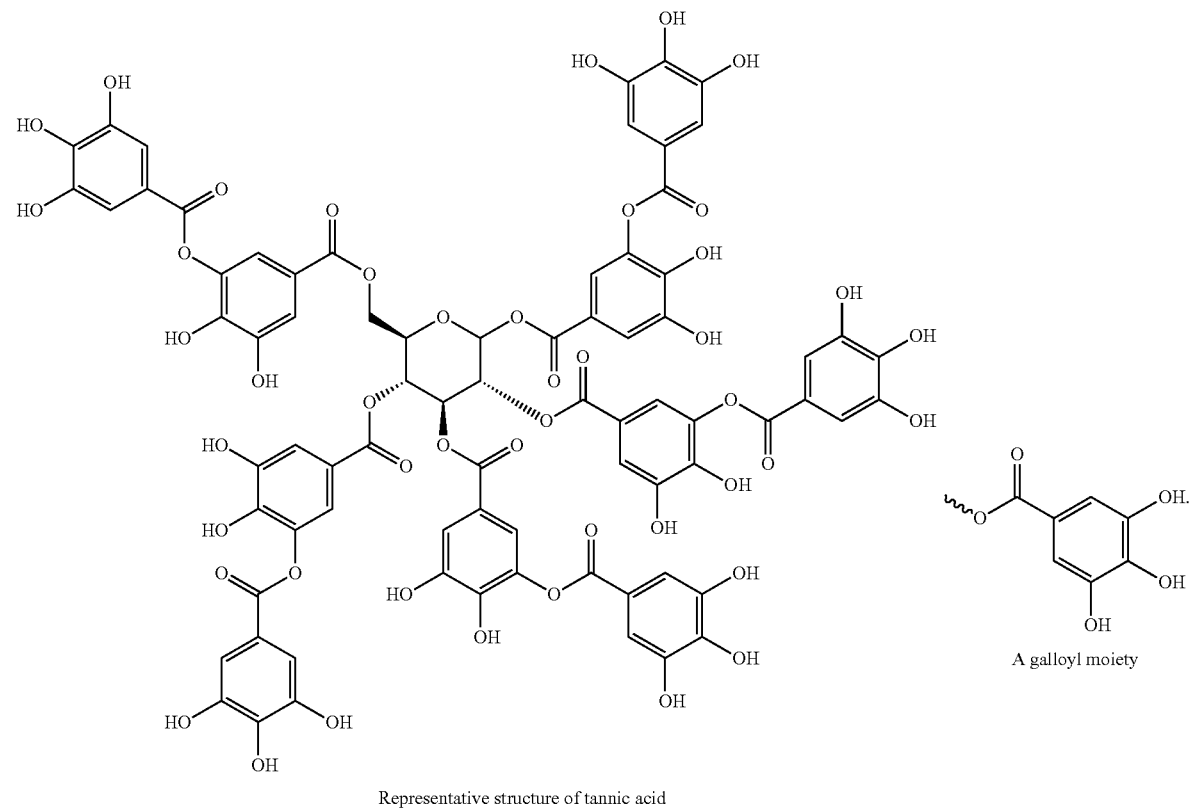

Representative structure of tannic acid

The above chemical formula is often given as $C_{76}H_{52}O_{46}$, which corresponds with decagalloyl glucose. However, commercially available tannic acid typically comprises a mixture of polygalloyl glucoses or polygalloyl quinic acid esters with the number of galloyl moieties per molecule ranging from 2 up to 20 (e.g., 2 to 15 and 2 to 12) and a molecular weight of 400 Daltons to 3500 Daltons (e.g., 496 to 3232 Daltons, 496 Daltons to 2472 Daltons, 180+152n Daltons, and 192+152n Daltons, in which n is between 2 and 13). Tannic acid has a weak acidity (e.g., pKa around 6) with a pH value of 2 to 5 (e.g., 3-4 and 2.5 to 3.5) in an aqueous solution containing 1% of tannic acid. Tannic acid has a water solubility of from 100 g/L to 2850 g/L (e.g., 250 g/L) at 25° C.

Tannic acid is usually extracted from any of the following plant parts: Tara pods (*Caesalpinia spinosa*), gallnuts from *Rhus semialata* or *Quercus infectoria* or Sicilian Sumac leaves (*Rhus coriaria*). Tannic acid is commercially available from suppliers such as Sigma-Aldrich (St Louis) and Ajinomoto OmniChem (Wetteren, Belgium) under the trademarks of Tanal® 01 (polygalloyl glucose, molecular weight 1440 Daltons), Tanal® 02 (polygalloyl glucose, molecular weight 1040 Daltons), and Tanal® 04 (polygalloyl quinic acid ester, molecular weight 860 Daltons).

In additional to polyphenols, other polyols can also be used. See polyols described in WO 2015/023961. Examples include pentaerythritol, dipentaerythritol, glycerol, polyglycerol, ethylene glycol, polyethylene glycol, trimethylolpropane, neopentyl glycol, sorbitol, erythritol, threitol, arabitol, xylitol, ribitol, mannitol, galactitol, fucitol, iditol, inositol, volemitol, isomalt, maltitol, lactitol, maltotriitol, maltotetraitol, polyglycitol, polyphenol, and combinations thereof.

Capsule Formation Aids

The microcapsule composition is typically prepared in the presence of a capsule formation aid, which can be a surfactant or dispersant. Capsule formation aids also improve the performance of the microcapsule composition. Performance is measured by the intensity of the fragrance released during certain stages, e.g., the pre-rub and post-rub phases in laundry applications. The pre-rub phase is the phase when the capsules have been deposited on the cloth, e.g., after a wash cycle using a capsule-containing fabric softener or detergent. The post-rub phase is after the capsules have been deposited and broken by friction or other mechanisms.

In some embodiments, the capsule formation aid is a protective colloid or emulsifier including, e.g., maleic-vinyl copolymers such as the copolymers of vinyl ethers with maleic anhydride or acid, sodium lignosulfonates, maleic anhydride/styrene copolymers, ethylene/maleic anhydride copolymers, and copolymers of propylene oxide and ethylene oxide, polyvinylpyrrolidone (PVP), polyvinyl alcohols (PVA), sodium salt of naphthalene sulfonate condensate, carboxymethyl cellulose (CMC), fatty acid esters of polyoxyethylenated sorbitol, sodium dodecylsulfate, and combinations thereof. The concentration of the capsule formation aid (e.g., the surfactant and dispersant) varies from 0.1% to 5% (e.g., 0.2% to 4%, 0.5% to 4%, 0.5% to 2.5%, and 1% to 2%) by weight of the capsule composition.

Commercially available surfactants include, but are not limited to, sulfonated naphthalene-formaldehyde condensates such as MORWET® D-425 (sodium salt of alkylnaphthalenesulfonate formaldehyde condensate, commercially available from Akzo Nobel, Fort Worth, Texas): partially hydrolyzed polyvinyl alcohols under the trade names of MOWIOL®, e.g., MOWIOL® 3-83 (commercially available from Kuraray, Houston, Texas); ethylene oxide-propylene oxide block copolymers or poloxamers such as PLURONIC®, SYNPERONIC® or PLURACARE® (BASF): sulfonated polystyrenes such as FLEXAN® II (Akzo Nobel): ethylene-maleic anhydride polymers such as ZEMAC® (Vertellus Specialties Inc., Indianapolis, Indiana); and Polyquaternium series such as Polyquaternium 11 ("PQ11;" a copolymer of vinyl pyrrolidone and quaternized dimethylaminoethyl methacrylate: sold by BASF as LUVI-QUAT® PQ11 AT 1).

Processing aids can also be used as capsule formation aids. They include hydrocolloids, which improve the colloidal stability of the slurry against coagulation, sedimentation and creaming. The term "hydrocolloid" refers to a broad class of water-soluble or water-dispersible polymers having anionic, cationic, zwitterionic or non-ionic character. Hydrocolloids useful in the present invention include, but are not limited to, polycarbohydrates, such as starch, modified starch, dextrin, maltodextrin, and cellulose derivatives, and their quaternized forms: natural gums such as alginate esters, carrageenan, xanthanes, agar-agar, pectines, pectic acid, and natural gums such as gum arabic, gum tragacanth and gum karaya, guar gums and quaternized guar gums: gelatine, protein hydrolysates and their quaternized forms; synthetic polymers and copolymers, such as poly(vinyl pyrrolidone-co-vinyl acetate), poly(vinyl alcohol-co-vinyl acetate), poly((met)acrylic acid), poly(maleic acid), poly(alkyl(meth)acrylate-co-(meth)acrylic acid), poly(acrylic acid-co-maleic acid)copolymer, poly(alkyleneoxide), poly(vinyl-methylether), poly(vinylether-co-maleic anhydride), and the like, as well as poly-(ethyleneimine), poly((meth)acrylamide), poly (alkyleneoxide-co-dimethylsiloxane), poly(amino dimethylsiloxane), and the like, and their quaternized forms.

The capsule formation aid may also be used in combination with carboxymethyl cellulose ("CMC"), polyvinylpyrrolidone, polyvinyl alcohol, alkylnaphthalenesulfonate formaldehyde condensates, and/or a surfactant during processing to facilitate capsule formation. Examples of these surfactants include cetyl trimethyl ammonium chloride (CTAC), poloxamers under the trade name of PLURONIC® (e.g., PLURONIC® F127), PLURAFAC® (e.g., PLURAFAC® F127), or MIRANET-N®, saponins such as QNATURALE® (National Starch Food Innovation): or a gum Arabic such as Seyal or Senegal. In certain embodiments, the CMC polymer has a molecular weight (e.g., weight average molecular weight) range between 90,000 Daltons to 1,500,000 Daltons, preferably between 250,000 Daltons to 750,000 Daltons and more preferably between 400,000 Daltons to 750,000 Daltons. The CMC polymer has a degree of substitution between 0.1 to 3, preferably between 0.65 to 1.4, and more preferably between 0.8 to 1. The CMC polymer is present in the capsule slurry at a level from 0.1% to 2% and preferably from 0.3% to 0.7%. In other embodiments, polyvinylpyrrolidone used in this invention is a water-soluble polymer and has a molecular weight (e.g., weight average molecular weight) of 1,000 Daltons to 10,000,000 Daltons. Suitable polyvinylpyrrolidones are polyvinylpyrrolidones K12, K15, K17, K25, K30, K60, K90, or a mixture thereof. The amount of the polyvinylpyrrolidone is 2% to 50%, 5% to 30%, or 10% to 25% by weight of the microcapsule composition.

Catalysts

In sometime embodiments, a catalyst is added to facilitate the formation of a capsule wall. Examples include metal carbonates, metal hydroxide, amino or organometallic compounds and include, for example, sodium carbonate, cesium carbonate, potassium carbonate, lithium hydroxide, 1,4-diazabicyclo[2.2.2]octane (i.e., DABCO), N,N-dimethylaminoethanol, N,N-dimethylcyclohexylamine, bis-(2-dimethylaminoethyl) ether, N,N dimethylacetylamine, stannous octoate, and dibutyltin dilaurate. In other embodiments, the catalyst is added to the oil-in-water emulsion to reduce undesired residuals such as isocyanates and amines.

Other Encapsulating Polymers

The microcapsule composition of this invention optionally has a second, third, fourth, fifth, or sixth microcapsule each formed of an encapsulating polymer selected from the group consisting of a sol-gel polymer (e.g., silica), polyacrylate, polyacrylamide, poly(acrylate-co-acrylamide), polyurea, polyurethane, starch, gelatin and gum Arabic, poly(melamine-formaldehyde), poly(urea-formaldehyde), and combinations thereof. A branched polyethyleneimine and its derivatives can also be coated onto the microcapsule wall to prepare a microcapsule having a positive zeta potential.

These encapsulating polymers are described in detail below.

Sol-gel Microcapsules. These microcapsules have a microcapsule wall formed of a sol-gel polymer, which is a reaction product of a sol-gel precursor via a polymerization reaction (e.g., hydrolyzation). Suitable sol-gel precursors are compounds capable of forming gels such as compounds containing silicon, boron, aluminum, titanium, zinc, zirconium, and vanadium. Preferred precursors are organosilicon, organoboron, and organoaluminum including metal alkoxides and b-diketonates.

Sol-gel precursors suitable for the purposes of the invention are selected in particular from the group of di-, tri- and/or tetrafunctional silicic acid, boric acid and alumoesters, more particularly alkoxysilanes (alkyl orthosilicates), and precursors thereof.

One example of sol-gel precursors suitable for the purposes of the invention are alkoxysilanes corresponding to the following general formula:

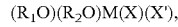

$(R_1O)(R_2O)M(X)(X')$, wherein X can be hydrogen or —$OR_3$; X' can be hydrogen or —$OR_4$; and $R_1$, $R_2$, $R_3$ and $R_4$ independently represent an organic group, more particularly a linear or branched alkyl group, preferably a $C_1$-$C_{12}$ alkyl. M can be Si, Ti, or Zr.

A preferred sol/gel precursor is alkoxysilanes corresponding to the following general formula: $(R_1O)(R_2O)Si(X)(X')$, wherein each of X, X', $R_1$, and $R_2$ are defined above.

Particularly preferred compounds are the silicic acid esters such as tetramethyl orthosilicate (TMOS) and tetraethyl orthosilicate (TEOS). A preferred compound includes Dynasylan® (organofunctional silanes commercially available from Degussa Corporation, Parsippany New Jersey, USA). Other sol-gel precursors suitable for the purposes of the invention are described, for example, in German Patent Application DE10021165. These sol-gel precursors are various hydrolyzable organosilanes such as, for example, alkylsilanes, alkoxysilanes, alkyl alkoxysilanes and organoalkoxysilanes. Besides the alkyl and alkoxy groups, other organic groups (for example allyl groups, aminoalkyl groups, hydroxyalkyl groups, etc.) may be attached as substituents to the silicon.

Recognizing that metal and semi metal alkoxide monomers (and their partially hydrolyzed and condensed polymers) such as tetramethoxy silane (TMOS), tetraethoxy silane (TEOS), etc. are very good solvents for numerous molecules and active ingredients is highly advantageous since it facilitates dissolving the active materials at a high concentration and thus a high loading in the final capsules.

Polyacrylate microcapsules, polyacrylamide microcapsules, and poly(acrylate-co-acrylamide) microcapsules. These microcapsules are prepared from corresponding precursors, which form the microcapsule wall. Preferred precursor are bi- or polyfunctional vinyl monomers including by way of illustration and not limitation, allyl methacrylate/acrylamide, triethylene glycol dimethacrylate/acrylamide, ethylene glycol dimethacrylate/acrylamide, diethylene glycol dimethacrylate/acrylamide, triethylene glycol dimethacrylate/acrylamide, tetraethylene glycol dimethacrylate/acrylamide, propylene glycol dimethacrylate/acrylamide, glycerol dimethacrylate/acrylamide, neopentyl glycol dimethacrylate/acrylamide, 1,10-decanediol dimethacrylate/acrylamide, pentaerythritol trimethacrylate/acrylamide, pentaerythritol tetramethacrylate/acrylamide, dipentaerythritol hexamethacrylate/acrylamide, triallyl-formal trimethacrylate/acrylamide, trimethylol propane trimethacrylate/acrylamide, tributanediol dimethacrylate/acrylamide, aliphatic or aromatic urethane diacrylates/acrylamides, difunctional urethane acrylates/acrylamides, ethoxylated aliphatic difunctional urethane methacrylates/acrylamides, aliphatic or aromatic urethane dimethacrylates/acrylamides, epoxy acrylates/acrylamides, epoxymethacrylates/acrylamides, 1,3-butylene glycol diacrylate/acrylamide, 1,4-butanediol dimethacrylate/acrylamide, 1,4-butaneidiol diacrylate/acrylamide, diethylene glycol diacrylate/acrylamide, 1,6-hexanediol diacrylate/acrylamide, 1,6-hexanediol dimethacrylate/acrylamide, neopentyl glycol diacrylate/acrylamide, polyethylene glycol diacrylate/acrylamide, tetraethylene glycol diacrylate/acrylamide, triethylene glycol diacrylate/acrylamide, 1,3-butylene glycol dimethacrylate/acrylamide, tripropylene glycol diacrylate/acrylamide, ethoxylated bisphenol diacrylate/acrylamide, ethoxylated bisphenol dimethylacrylate/acrylamide, dipropylene glycol diacrylate/acrylamide, alkoxylated hexanediol diacrylate/acrylamide, alkoxylated cyclohexane dimethanol diacrylate/acrylamide, propoxylated neopentyl glycol diacrylate/acrylamide, trimethylol-propane triacrylate/acrylamide, pentaerythritol triacrylate/acrylamide, ethoxylated trimethylolpropane triacrylate/acrylamide, propoxylated trimethylolpropane triacrylate/acrylamide, propoxylated glyceryl triacrylate/acrylamide, ditrimethylolpropane tetraacrylate/acrylamide, dipentaerythritol pentaacrylate/acrylamide, ethoxylated pentaerythritol tetraacrylate/acrylamide, PEG 200 dimethacrylate/acrylamide, PEG 400 dimethacrylate/acrylamide, PEG 600 dimethacrylate/acrylamide, 3-acryloyloxy glycol monoacrylate/acrylamide, triacryl formal, triallyl isocyanate, and triallyl isocyanurate.

The monomer is typically polymerized in the presence of an activation agent (e.g., an initiator) at a raised temperature (e.g., 30-90° C.) or under UV light. Exemplary initiators are 2,2'-azobis(isobutyronitrile) ("AIBN"), dicetyl peroxydicarbonate, di(4-tert-butylcyclohexyl) peroxydicarbonate, dioctanoyl peroxide, dibenzoyl peroxide, dilauroyl peroxide, didecanoyl peroxide, tert-butyl peracetate, tert-butyl perlaurate, tert-butyl perbenzoate, tert-butyl hydroperoxide, cumene hydroperoxide, cumene ethylperoxide, diisopropylhydroxy dicarboxylate, 2,2'-azobis(2,4-dimethylvaleronitrile), 1, 1'-azobis-(cyclohexane-1-carbonitrile), dimethyl 2,2'-azobis(2-methylpropionate), 2,2'-azobis[2-methyl-N-(2-hydroxyethyl) propionamide, sodium persulfate, benzoyl peroxide, and combinations thereof.

Emulsifiers used in the formation of these capsule walls are typically anionic emulsifiers including without limitation, water-soluble salts of alkyl sulfates, alkyl ether sulfates, alkyl isothionates, alkyl carboxylates, alkyl sulfosuccinates, alkyl succinamates, alkyl sulfate salts such as sodium dodecyl sulfate, alkyl sarcosinates, alkyl derivatives of protein hydrolyzates, acyl aspartates, alkyl or alkyl ether or alkylaryl ether phosphate esters, sodium dodecyl sulphate, phospholipids or lecithin, or soaps, sodium, potassium or ammonium stearate, oleate or palmitate, alkylarylsulfonic acid salts such as sodium dodecylbenzenesulfonate, sodium dialkylsulfo-succinates, dioctyl sulfosuccinate, sodium dilaurylsulfosuccinate, poly (styrene sulfonate) sodium salt, isobutylene-maleic anhydride copolymer, gum arabic, sodium alginate, carboxymethyl cellulose, cellulose sulfate and pectin, poly(styrene sulfonate), isobutylene-maleic anhydride copolymer, gum arabic, carrageenan, sodium alginate, pectic acid, tragacanth gum, almond gum and agar; semi-synthetic polymers such as carboxymethyl cellulose, sulfated cellulose, sulfated methylcellulose, carboxymethyl starch, phosphated starch, lignin sulfonic acid; and synthetic polymers such as maleic anhydride copolymers (including hydrolyzates thereof), polyacrylic acid, polymethacrylic acid, acrylic acid butyl acrylate copolymer or crotonic acid homopolymers and copolymers, vinylbenzenesulfonic acid or 2-acrylamido-2-methylpropane-sulfonic acid homopolymers and copolymers, and partial amide or partial ester of such polymers and copolymers, carboxy modified polyvinyl alcohol, sulfonic acid-modified polyvinyl alcohol and phosphoric acid-modified polyvinyl alcohol, phosphated or sulfated tristyrylphenol ethoxylates. The amount of anionic emulsifier is anywhere from 0.1% to 40% by weight of all constituents, more preferably from 0.5% to 10%, more preferably 0.5% to 5% by weight.

Aminoplasts and Gelatin. A representative process used for aminoplast encapsulation is disclosed in U.S. Pat. No. 3,516,941 and US 2007/0078071, though it is recognized that many variations with regard to materials and process steps are possible. Another encapsulation process, i.e., gelatin encapsulation, is disclosed in U.S. Pat. No. 2,800,457. Both processes are discussed in the context of fragrance encapsulation for use in consumer products in U.S. Pat. Nos. 4,145,184 and 5,112,688 respectively. Polymer systems are well-known in the art and non-limiting examples of these include aminoplast capsules and encapsulated particles as disclosed in GB 2006709 A; the production of microcapsules having walls comprising styrene-maleic anhydride reacted with melamine-formaldehyde precondensates as disclosed in U.S. Pat. No. 4,396,670; an acrylic acid-acrylamide copolymer, cross-linked with a melamine-formaldehyde resin as disclosed in U.S. Pat. No. 5,089,339; capsules composed of cationic melamine-formaldehyde condensates as disclosed in U.S. Pat. No. 5,401,577; melamine formaldehyde microencapsulation as disclosed in U.S. Pat. No. 3,074,845: amido-aldehyde resin in-situ polymerized capsules disclosed in EP 0 158 449 A1; etherified urea-formaldehyde polymer as disclosed in U.S. Pat. No. 5,204,185; melamine-formaldehyde microcapsules as described in U.S. Pat. No. 4,525,520; cross-linked oil-soluble melamine-formaldehyde precondensate as described in U.S. Pat. No. 5,011,634; capsule wall material formed from a complex of cationic and anionic melamine-formaldehyde precondensates that are then cross-linked as disclosed in U.S. Pat. No. 5,013,473; polymeric shells made from addition polymers such as condensation polymers, phenolic aldehydes, urea aldehydes or acrylic polymer as disclosed in U.S. Pat. No. 3,516,941; urea-formaldehyde capsules as disclosed in EP 0 443 428 A2; melamine-formaldehyde chemistry as disclosed in GB 2 062 570 A; and capsules composed of polymer or copolymer of styrene sulfonic acid in acid of salt form, and capsules cross-linked with melamine-formaldehyde as disclosed in U.S. Pat. No. 4,001,140.

Urea-formaldehyde and melamine-formaldehyde Capsules. Urea-formaldehyde and melamine-formaldehyde pre-condensate capsule shell wall precursors are prepared by means of reacting urea or melamine with formaldehyde where the mole ratio of melamine or urea to formaldehyde is in the range of from 10:1 to 1:6, preferably from 1:2 to 1:5. For purposes of practicing this invention, the resulting material has a molecular weight in the range of from 156 Da to 3000 Da. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine/urea:formaldehyde:alkanol is in the range of 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. No. 6,261,483, and Lee et al. (2002) *J. Microencapsulation* 19, 559-569.

Examples of urea-formaldehyde pre-condensates useful in the practice of this invention are URAC™ 180 and URAC™ 186, trademarks of Cytec Technology Corp. of Wilmington, DE. Examples of melamine-formaldehyde pre-condensates useful in the practice if this invention, include, but are not limited to, CYMEL® U-60, CYMEL® U-64 and CYMEL® U-65, trademarks of Cytec Technology Corp. of Wilmington, DE. It is preferable to use, as the precondensate for cross-linking, the substituted or un-substituted acrylic acid polymer or co-polymer. In practicing this invention, the range of mole ratios of urea-formaldehyde precondensate/melamine-formaldehyde pre-condensate to substituted/un-substituted acrylic acid polymer/co-polymer is in the range of from 9:1 to 1:9, preferably from 5:1 to 1:5 and most preferably from 2:1 to 1:2.

In one embodiment of the invention, microcapsules with polymer(s) composed of primary and/or secondary amine reactive groups or mixtures thereof and cross-linkers can also be used. See US 2006/0248665. The amine polymers can possess primary and/or secondary amine functionalities and can be of either natural or synthetic origin. Amine-containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN® series of polyvinyl formamides available from BASF. The molecular weights of these materials can range from 10,000 Da to 1,000,000 Da.

These capsules can also include formaldehyde scavengers, which are capable of binding free formaldehyde. When the capsules are for use in aqueous media, formaldehyde scavengers such as sodium sulfite, melamine, glycine, and carbohydrazine are suitable. When the capsules are aimed to be used in products having low pH, e.g., fabric care conditioners, formaldehyde scavengers are preferably selected from beta diketones, such as beta-ketoesters, or from 1,3-diols, such as propylene glycol. Preferred beta-ketoesters include alkyl-malonates, alkyl aceto acetates and polyvinyl alcohol aceto acetates.

The microcapsule composition of this invention optionally contains one or more additional microcapsules, e.g., a second, third, fourth, fifth, or sixth microcapsules. Each of these microcapsules can be any of the microcapsule described above.

These additional microcapsules can be any microcapsules described above but different from each other in term of microcapsule size, degree of polymerization, degree of crosslinking, encapsulating polymer, thickness of the wall, active material, ratio between the wall material and the active material, rupture force or fracture strength, and the like.

Active Materials

The microcapsule core can include one or more active materials including flavors and/or fragrance ingredients such as fragrance oils. Individual active materials that can be encapsulated include those listed in WO 2016049456, pages 38-50. These active material include flavor or fragrance ingredients, taste masking agents, taste sensates, malodor counteracting agents, vitamins or derivatives thereof, anti-bacterials, sunscreen actives, antioxidants, anti-inflammatory agents, fungicide, anesthetics, analgesics, antifungal agents, antibiotics, anti-viral agents, anti-parasitic agents, anti-infectious, anti-acne agents, dermatological active ingredients, enzymes and co-enzymes, skin whitening agents, anti-histamines, chemotherapeutic agents, insect repellents, emollient, skin moisturizing agent, wrinkle control agent, UV protection agent, fabric softener active, hard surface cleaning active, skin or hair conditioning agent, animal repellent, vermin repellent, flame retardant, antistatic agent, nanometer to micron size inorganic solid, polymeric or elastomeric particle, and combination thereof.

High performing, high impact fragrances are envisaged. One class of high performing fragrances is described in WO 2018/071897. These fragrances have a high intensity accord containing (i) at least 7 wt % (e.g., 7 to 95 wt %) of Class 1 fragrance ingredients, (ii) 5 to 95 wt % (e.g., 5 to 80 wt %, 10 to 80 wt %, and 10 to 70 wt %) of Class 2 fragrance ingredients, and (iii) 0 to 80 wt % of Class 3 fragrance ingredients, in which the Class 1 fragrance ingredients each have an experimental velocity of 8.5 cm/second or greater, the Class 2 fragrance ingredients each have an experimental velocity of less than 8.5 cm/second and greater than 5 cm/second, and the Class 3 fragrance ingredients each have an experimental velocity of 5 cm/second or less. In some embodiments, the sum of the Class 1 fragrance ingredients, the Class 2 fragrance ingredients, and the Class 3 fragrance ingredients is 100%. In other embodiments, the sum of Class 1 and Class 2 ingredients is 20% to 100 wt %. Other high impact fragrances suitable for use in this invention are those described in WO 1999/065458, U.S. Pat. No. 9,222,055, US 2005/0003975, and WO1997/034987.

In addition to the active materials listed above, the products of this invention can also contain, for example, the following dyes, colorants or pigments: lactoflavin (riboflavin), beta-carotene, riboflavin-5'-phosphate, alpha-carotene, gamma-carotene, cantaxanthin, erythrosine, curcumin, quinoline yellow, yellow orange S, tartrazine, bixin, norbixin (annatto, orlean), capsanthin, capsorubin, lycopene, beta-apo-8'-carotenal, beta-apo-8'-carotenic acid ethyl ester, xanthophylls (flavoxanthin, lutein, cryptoxanthin, rubixanthin, violaxanthin, rodoxanthin), fast carmine (carminic acid, cochineal), azorubin, cochineal red A (Ponceau™ 4 R), beetroot red, betanin, anthocyanins, amaranth, patent blue V, indigotine I (indigo-carmine), chlorophylls, copper compounds of chlorophylls, acid brilliant green BS (lissamine green), brilliant black BN, vegetable carbon, titanium dioxide, iron oxides and hydroxides, calcium carbonate, aluminum, silver, gold, pigment rubine BK (lithol rubine BK), methyl violet B, victoria blue R, victoria blue B, acilan brilliant blue FFR (brilliant wool blue FFR), naphthol green B, acilan fast green 10 G (alkali fast green 10 G), ceres yellow GRN, sudan blue II, ultramarine, phthalocyanine blue, phthalocayanine green, fast acid violet R. Further naturally obtained extracts (for example paprika extract, black carrot extract, red cabbage extract) can be used for coloring purposes. Goods results are also achieved with the colors named in the following, the so-called aluminum lakes: FD & C Yellow 5 Lake, FD & C Blue 2 Lake, FD & C Blue 1 Lake, Tartrazine Lake, Quinoline Yellow Lake, FD & C Yellow 6 Lake, FD & C Red 40 Lake, Sunset Yellow Lake, Carmoisine Lake, Amaranth Lake, Ponceau 4R Lake, Erythrosyne Lake, Red 2G Lake, Allura Red Lake, Patent Blue V Lake, Indigo Carmine Lake, Brilliant Blue Lake, Brown HT Lake, Black PN Lake, Green S Lake and mixtures thereof.

When the active material is a fragrance, it is preferred that fragrance ingredients within a fragrance having a ClogP of 0.5 to 15 are employed. For instance, the ingredients having a ClogP value between 0.5 to 8 (e.g., between 1 to 12, between 1.5 to 8, between 2 and 7, between 1 and 6, between 2 and 6, between 2 and 5, between 3 and 7) are 25% or greater (e.g., 50% or greater and 90% or greater) by the weight of the fragrance.

It is preferred that a fragrance having a weight-averaged ClogP of 2.5 and greater (e.g., 3 or greater, 2.5 to 7, and 2.5 to 5) is employed. The weight-averaged ClogP is calculated as follows:

$$\text{ClogP} = \{\text{Sum}[(W_i)(\text{ClogP})_i]\} / \{\text{Sum } W_i\},$$

in which $W_i$ is the weight fraction of each fragrance ingredient and $(\text{ClogP})_i$ is the ClogP of that fragrance ingredient.

As an illustration, it is preferred that greater than 60 wt % (preferably greater than 80 wt % and more preferably greater than 90 wt %) of the fragrance chemicals have ClogP values of greater than 2 (preferably greater than 3.3, more preferably greater than 4, and even more preferably greater than 4.5).

Those with skill in the art will appreciate that many fragrances can be created employing various solvents and fragrance chemicals. The use of a relatively low to intermediate ClogP fragrance ingredients will result in fragrances that are suitable for encapsulation. These fragrances are generally water-insoluble, to be delivered through the capsule systems of this invention onto consumer products in different stages such as damp and dry fabric. Without encapsulation, the free fragrances would normally have evaporated or dissolved in water during use, e.g., wash. Though high ClogP materials are generally well delivered from a regular (non-encapsulated) fragrance in a consumer product, they have excellent encapsulation properties and are also suitable for encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

In some embodiments, the amount of encapsulated active material is from 5% to 95% (e.g., 10% to 90%, 15% to 80%, and 20% to 60%) by weight of the microcapsule composition. The amount of the capsule wall is from 0.5% to 30% (e.g., 1% to 25%, 2 to 20% and 5 to 15%) also by weight of the microcapsule composition. In other embodiments, the amount of the encapsulated active material is from 15% to 99.5% (e.g., 20% to 98% and 30% to 90%) by weight of the microcapsule, and the amount of the capsule wall is from 0.5% to 85% (e.g., 2 to 50% and 5 to 40%) by weight of the microcapsule.

Adjunct Materials

In addition to the active materials, the present invention also contemplates the incorporation of adjunct materials including solvent, emollients, and core modifier materials in the core encapsulated by the capsule wall. Other adjunct materials are solubility modifiers, density modifiers, stabilizers, viscosity modifiers, pH modifiers, or any combination thereof. These modifiers can be present in the wall or core of the capsules, or outside the capsules in delivery system. Preferably, they are in the core as a core modifier.

The one or more adjunct material may be added in the amount of 0.01% to 40% (e.g., 0.5% to 30%) by weight of the microcapsule.

Suitable examples include those described in WO 2016/049456, pages 55-57 and US 2016/0158121, pages 15-18.

Deposition Aids

An exemplary deposition aid useful in the microcapsule composition of this invention is a copolymer of acrylamide and acrylamidopropyltrimonium chloride. This copolymer facilitates the deposition of the microcapsule onto a hard surface (e.g., hair, skin, fiber, furniture, and floor). The copolymer generally has an average molecular weight (e.g., weight average molecular mass (Mw) determined by size exclusion chromatography) of 2,000 Da to 10,000,000 Da with a lower limit of 2,000 Da, 5,000 Da, 10,000 Da, 20,000 Da, 50,000 Da, 100,000 Da, 250,000 Da, 500,000 Da, or 800,000 Da and an upper limit of 10,000,000 Da, 5,000,000 Da, 2,000,000 Da, 1,000,000 Da, or 500,000 Da (e.g., 500,000 Da to 2,000,000 Da and 800,000 Da to 1,500,000 Da). The charge density of the copolymer ranges from 1 meq/g to 2.5 meq/g, preferably from 1.5 meq/g to 2.2 meq/g. The copolymer of acrylamide and acrylamide-propyltrimonium chloride is commercially available from various vendors such as Ashland as N-Hance® SP-100 and Ciba SAL-CARE® SC60.

Other suitable deposition aids include anionically, cationically, nonionically, or amphoteric water-soluble polymers. Suitable deposition aids include chitosan, polyquaternium-4, polyquaternium-5, polyquaternium-6, polyquaternium-7, polyquaternium-10, polyquaternium-11, polyquaternium-16, polyquaternium-22, polyquaternium-24, polyquaternium-28, polyquaternium-37, polyquaternium-39, polyquaternium-44, polyquaternium-46, polyquaternium-47, polyquaternium-53, polyquaternium-55, polyquaternium-67, polyquaternium-68, polyquaternium-69, polyquaternium-73, polyquaternium-74, polyquaternium-77, polyquaternium-78, polyquaternium-79, polyquaternium-80, polyquaternium-81, polyquaternium-82, polyquaternium-86, polyquaternium-88, polyquaternium-101, polyvinylamine, polyethyleneimine, polyvinylamine and vinylformamide copolymer, a methacrylamidopropyltrimonium chloride/acrylamide copolymer, copolymer of acrylamide and acrylamidopropyltrimonium chloride, 3-acrylamidopropyl trimethylammonium polymer or its copolymer, diallyldimethylammoniumchloride polymer and its copolymer, a polysaccharide with saccharide unit functionalized with hydroxypropyl trimonium, and combinations thereof. More examples of the deposition aid are described in WO 2016049456, pages 13-27; US 2013/0330292; US 2013/0337023; and US 2014/0017278.

Additional depositional aids are those cationic polymers described in WO2016032993. These cationic polymers are typically characterized by a relatively high charge density (e.g., from 4 meq/g, or from 5 meq/g, or from 5.2 meq/g to 12 meq/g, or to 10 meq/g, or to 8 meq/g or to 7 meq/g, or to 6.5 meq/g. The cationic polymers are comprised of structural units that are nonionic, cationic, anionic, or mixtures thereof. In some aspects, the cationic polymer comprises from 5 mol % to 60 mol %, or from 15 mol % to 30 mol %, of a nonionic structural unit derived from a monomer selected from the group consisting of (meth)acrylamide, vinyl formamide, N,N-dialkyl acrylamide, N,N-dialkylmethacrylamide, $C_1$-$C_{12}$ alkyl acrylate, $C_1$-$C_{12}$ hydroxyalkyl acrylate, polyalkylene glyol acrylate, $C_1$-$C_{12}$ alkyl methacrylate, $C_1$-$C_{12}$ hydroxyalkyl methacrylate, polyalkylene glycol methacrylate, vinyl acetate, vinyl alcohol, vinyl formamide, vinyl acetamide, vinyl alkyl ether, vinyl pyridine, vinyl pyrrolidone, vinyl imidazole, vinyl caprolactam, and mixtures thereof.

In some aspects, the cationic polymer comprises a cationic structural unit at the level of 30 mol % to 100 mol %, or 50 mol % to 100 mol %, or 55 mol % to 95 mol %, or 70 mol % to 85 mol % by mass of the cationic polymer. The cationic structural unit is typically derived from a cationic monomer such as N,N-dialkylaminoalkyl methacrylate, N,N-dialkylaminoalkyl acrylate, N,N-dialkylaminoalkyl acrylamide, N,N-dialkylaminoalkylmethacrylamide, methacylamidoalkyl trialkylammonium salts, acrylamidoalkylltrialkylamminium salts, vinylamine, vinylimine, vinyl imidazole, quaternized vinyl imidazole, diallyl dialkyl ammonium salts, and mixtures thereof. Preferably, the cationic monomer is selected from the group consisting of diallyl dimethyl ammonium salts (DADMAS), N,N-dimethyl aminoethyl acrylate, N,N-dimethyl aminoethyl methacrylate (DMAM), [2-(methacryloylamino)ethyl]tri-methylammonium salts, N,N-dimethylaminopropyl acrylamide (DMAPA), N,N-dimethylaminopropyl methacrylamide (DMAPMA), acrylamidopropyl trimethyl ammonium salts (APTAS), methacrylamidopropyl trimethylammonium salts (MAPTAS), quaternized vinylimidazole (QVi), and mixtures thereof.

In some aspects, the cationic polymer comprises an anionic structural unit at a level of 0.01 mol % to 15 mol %, 0.05 mol % to 10 mol %, 0.1 mol % to 5 mol %, or 1% to 4% of by mass of the cationic polymer. In some aspects, the anionic structural unit is derived from an anionic monomer selected from the group consisting of acrylic acid (AA), methacrylic acid, maleic acid, vinyl sulfonic acid, styrene sulfonic acid, acrylamidopropylmethane sulfonic acid (AMPS) and their salts, and mixtures thereof.

Exemplary cationic polymers are polyacrylamide-co-DADMAS, polyacrylamide-co-DADMAS-co-acrylic acid, polyacrylamide-co-APTAS, polyacrylamide-co-MAPTAS, polyacrylamide-co-QVi, polyvinyl formamide-co-DADMAS, poly(DADMAS), polyacrylamide-co-MAPTAS-coacrylic acid, polyacrylamide-co-APTAS-co-acrylic acid, and mixtures thereof.

The deposition aid is generally present at a level of 0.01% to 50% (with a lower limit of 0.01%, 0.05%, 0.1%, 0.5%, 1%, 2%, or 5% and an upper limit of 50%, 40%, 30%, 20%, 15%, or 10%, e.g., 0.1% to 30%, 1% to 20%, 2% to 15%, and 5% to 10%) by weight of the microcapsule composition. In a consumer product such as a shampoo, the deposition aid is generally present at a level of 0.001% to 20% (with a lower limit of 0.001%, 0.005%, 0.01%, 0.02%, or 0.05% and an upper limit of 20%, 15%, 10%, 5%, 2%, or 1%, e.g., 0.005% to 10%, 0.01% to 5%, and 0.02% to 0.5%) by weight of the shampoo composition. The capsule deposition aid can be added during the preparation of the microcapsules or it can be added after the microcapsules have been made.

A second capsule deposition aid from 0.01% to 25%, more preferably from 5% to 20% can be added to the microcapsule composition. The second capsule formation deposition aid can be selected from the above-described deposition aid.

Additional Components

The microcapsule composition of this invention can include one or more non-confined or unencapsulated active materials from 0.01 to 50%, more preferably from 5 to 40%.

The capsule delivery system can also contain one or more other delivery system such as polymer-assisted delivery compositions (see U.S. Pat. No. 8,187,580), fiber-assisted delivery compositions (US 2010/0305021), cyclodextrin host guest complexes (U.S. Pat. No. 6,287,603 and US 2002/0019369), pro-fragrances (WO 2000/072816 and EP 0 922 084), and any combination thereof. More exemplary delivery systems that can be incorporated are coacervate capsules, cyclodextrin delivery systems, and pro-perfumes.

Examples of additional components include those described in US 2016/0158121.

Any compound, polymer, or agent discussed above can be the compound, polymer, or agent itself as shown above, or its salt, precursor, hydrate, or solvate. A salt can be formed between an anion and a positively charged group on the compound, polymer, or agent. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group on the compound, polymer, or agent. Suitable cations include sodium ion, potassium ion, magnesium ion, calcium ion, and an ammonium cation (e.g., tetramethyl-ammonium ion). A precursor can be ester and another suitable derivative, which, during the process of preparing a capsule composition of this invention, is capable of converting to the compound, polymer, or agent and being used in preparing the capsule composition. A hydrate refers to the compound, polymer, or agent that contains water. A solvate refers to a complex formed between the compound, polymer, or agent and a suitable solvent. A suitable solvent can be water, ethanol, isopropanol, ethyl acetate, acetic acid, and ethanolamine.

Certain compounds, polymers, and agents have one or more stereocenters, each of which can be in the R configuration, the S configuration, or a mixture. Further, some compounds, polymers, and agents possess one or more double bonds wherein each double bond exists in the E (trans) or Z (cis) configuration, or combinations thereof. The compounds, polymers, and agents include all possible configurational stereoisomeric, regioisomeric, diastereomeric, enantiomeric, and epimeric forms as well as any mixtures thereof. As such, lysine used herein includes L-lysine, D-lysine, L-lysine monohydrochloride, D-lysine monohydrochloride, lysine carbonate, and so on. Similarly, arginine includes L-arginine, D-arginine, L-arginine monohydrochloride, D-arginine monohydrochloride, arginine carbonate, arginine monohydrate, and etc. Guanidine includes guanidine hydrochloride, guanidine carbonate, guanidine thiocyanate, and other guanidine salts including their hydrates. Ornithine includes L-ornithine and its salts/hydrates (e.g., monohydrochloride) and D-ornithine and its salts/hydrates (e.g., monohydrochloride).

The microcapsule composition of this invention can be a slurry containing in a solvent (e.g., water) the capsule at a level 0.1% to 80% (preferably 1% to 65% and more preferably 5% to 45%) by weight of the capsule delivery system. An exemplary microcapsule composition of this invention contains a plurality of microcapsules each dispersed in an aqueous phase and is stable for at least 7 days (e.g., at least 10 days, at least 30 days, and at least 60 days) at 40° C. Stability is measured (e.g., in a graduated cylinder) by the separation of a clear aqueous phase from the microcapsule composition. The microcapsule composition is deemed stable if, by volume of the microcapsule composition, less than 10% of a clear aqueous phase is separated. The microcapsule composition is considered stable when (i) the composition has a viscosity of 3000 cP or less (e.g., 2000 cP or less) and (ii) 20% or less (e.g., 15% or less, and 10% or less) water by volume of the composition is separated from the composition. The volume of the separated water can be readily measured by a convention method, e.g., a graduated cylinder.

Microcapsule compositions are known to have the tendency to form into gels, unsuitable for use in many consumer products. The viscosity of the gelled-out composition increases to at least 3000 centipoise (cP) (e.g., at least 6000 cP). The viscosity can be readily measured on rheometer, for example a RheoStress™ 1 instrument (Commercially available from ThermoScientific), using rotating disks at a shear rate of $21\ s^{-1}$ and a temperature of 25° C.

In some embodiments, the microcapsule composition is purified by washing the capsule slurry with water until a neutral pH (pH of 6 to 8) is achieved. For the purposes of the present invention, the capsule suspension can be washed using any conventional method including the use of a separatory funnel, filter paper, centrifugation and the like. The capsule suspension can be washed one, two, three, four, five, six, or more times until a neutral pH, e.g., pH 6-8 and 6.5-7.5, is achieved. The pH of the purified capsules can be determined using any conventional method including, but not limited to pH paper, pH indicators, or a pH meter.

A capsule composition is "purified" in that it is 80%, 90%, 95%, 97%, 98% or 99% homogeneous to capsules. In accordance with the present invention, purity is achieved by washing the capsules until a neutral pH is achieved, which is indicative of removal of unwanted impurities and/or starting materials, e.g., polyisocyanate, cross-linking agent and the like.

In certain embodiments of this invention, the purification of the capsules includes the additional step of adding a salt to the capsule suspension prior to the step of washing the capsule suspension with water. Exemplary salts of use in this step of the invention include, but are not limited to, sodium chloride, potassium chloride or bi-sulphite salts. See US 2014/0017287.

The microcapsule composition of this invention can also be dried, e.g., spray dried, heat dried, and belt dried, to a solid form. In a spray drying process, a spray dry carrier is added to a microcapsule composition to assist the removal of water from the slurry. See US20120151790, US20140377446, US20150267964, US20150284189, and US20160097591.

According to one embodiment, the spray dry carriers can be selected from the group consisting of carbohydrates such as chemically modified starches and/or hydrolyzed starches, gums such as gum Arabic, proteins such as whey protein, cellulose derivatives, clays, synthetic water-soluble polymers and/or copolymers such as polyvinyl pyrrolidone, polyvinyl alcohol. The spray dry carriers may be present in an amount from 1 to 50%, more preferably from 5 to 20%, by weight of the microcapsule composition in slurry.

Optionally, a free flow agent (anticaking agent) of silicas which may be hydrophobic (i.e. silanol surface treated with halogen silanes, alkoxysilanes, silazanes, siloxanes, etc. such as Sipernat® D17, Aerosil® R972 and R974 (available from Degussa), etc.) and/or hydrophilic such as Aerosil®

200, Sipernat® 22S, Sipernat® 50S, (available from Degussa), Syloid® 244 (available from Grace Davison), may be present from 0.01 to 10%, more preferable from 0.5 to 5%, by weight of the microcapsule composition in slurry.

Humectants and viscosity control/suspending agents can also be added to facilitate spray drying. These agents are disclosed in U.S. Pat. Nos. 4,446,032 and 6,930,078. Details of hydrophobic silica as a functional delivery vehicle of active materials other than a free flow/anticaking agent are disclosed in U.S. Pat. Nos. 5,500,223 and 6,608,017.

The spray drying inlet temperature is in the range of 150 to 240° C., preferably between 17° and 230° C., more preferably between 19° and 220° C.

As described herein, the spray-dried microcapsule composition is well suited for use in a variety of all dry (anhydrous) products: powder laundry detergent, fabric softener dryer sheets, household cleaning dry wipes, powder dish detergent, floor cleaning cloths, or any dry form of personal care products (e.g. shampoo powder, deodorant powder, foot powder, soap powder, baby powder), etc. Because of high fragrance and/or active agent concentration in the spray-dried products of the present invention, characteristics of the aforementioned consumer dry products will not be adversely affected by a small dosage of the spray-dried products.

The microcapsule composition can also be sprayed as a slurry onto a consumer product, e.g., a fabric care product. By way of illustration, a liquid delivery system containing capsules is sprayed onto a detergent powder during blending to make granules. See US 2011/0190191. In order to increase fragrance load, water-absorbing material, such as zeolite, can be added to the delivery system.

Alternatively, granulates in a consumer product are prepared in a mechanical granulator in the presence of a granulation auxiliary such as non-acid water-soluble organic crystalline solids. See WO 2005/097962.

Zeta Potentials and Rupture Forces

The microcapsule of this invention is positively charged as indicated by a zeta potential of at least 10 mV, preferably at least 25 mV (e.g., 25 mV to 200 mV), and more preferably at least 40 mV (e.g., 40 mV to 100 mV).

Zeta potential is a measurement of electrokinetic potential in the microcapsule. From a theoretical viewpoint, zeta potential is the potential difference between the water phase (i.e., the dispersion medium) and the stationary layer of water attached to the surface of the microcapsule.

The zeta potential is an important indicator of the stability of the microcapsule in compositions or consumer products. Typically, a microcapsule having a zeta potential of 10 mV to 25 mV shows a moderate stability. Similarly, a microcapsule having a zeta potential of 25 mV to 40 m V shows a good stability and a microcapsule having a zeta potential of 40 mV to 100 mV shows excellent stability. Not to be bound by any theory, the microcapsule of this invention has a desirable zeta potential making it suitable for use in consumer products with improved stability.

The zeta potential can be calculated using theoretical models and an experimentally-determined electrophoretic mobility or dynamic electrophoretic mobility. The zeta potential is conventionally measured by methods such as microelectrophoresis, or electrophoretic light scattering, or electroacoustic phenomena. For more detailed discussion on measurement of zeta potential, see Dukhin and Goetz, "Ultrasound for characterizing colloids", Elsevier, 2002.

The microcapsule of this invention has a fracture strength of 0.2 MPa to 80 MPa (e.g., 0.5 MPa to 60 MPa, 1 MPa to 50 MPa, and 5 MPa to 30 MPa). The fracture strength of each microcapsule is calculated by dividing the rupture force (in Newtons) by the cross-sectional area of the respective microcapsule ($\pi r^2$, where r is the radius of the particle before compression). The measurement of the rupture force and the cross-sectional area is performed following the methods described in Zhang et al., *J. Microencapsulation* 18 (5), 593-602 (2001).

The microcapsule of this invention has a rupture force of less than 10 millinewtons ("mN") such as 0.1 mN to 10 mN, 0.2 mN to 8 mN, 0.3 mN to 5 mN, 0.1 mN to 2 mN, 0.1 mN, 0.5 mN, 1 mN, 2 mN, 5 mN, and 8 mN. The rupture force is the force needed to rupture the microcapsules. Its measurement is based on a technique known in the art as micro-manipulation. See Zhang et al., *Journal of Microencapsulation* 16 (1), 117-124 (1999).

Applications.

The microcapsule composition of this invention can be added to a consumer product base directly or be printed onto a product base or a movable product conveyor (e.g., a non-stick belt) for drying. See International Application Publication WO2019212896A1. In a typical printing system, the microcapsule composition is printed onto a movable product conveyor that directly receives the printed microcapsule, which is then dried on the movable product conveyor to produce a dried product. Additional carriers and solvent can be added to the microcapsule composition before printing. In some embodiments, the viscosity of the microcapsule composition is adjusted to more than 500 cP or more than 1000 cP with a viscosity modifier. With reference to the print assembly, the print assembly can include a print head or array of nozzles and optionally be adapted to print the microcapsule in a dot pattern (e.g., arranged to facilitate drying, post-processing, and product quality). Optional features of the system include, a dehumidifier configured to supply desiccated air to the drying component: a supplemental energy source (e.g. a radiant heat source), for facilitating drying of the printed microcapsule; and/or a product discharge component for removing dried product from the movable product conveyor.

The microcapsule of the present invention is well-suited for use, without limitation, in the following products:
a) Household products
  i. Liquid or Powder Laundry Detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818
  ii. Unit Dose Pouches, Tablets and Capsules such as those described in EP 1 431 382 A1, US 2013/0219996 A1, US 2013/0284637 A1, and U.S. Pat. No. 6,492,315. These unit dose formulations can contain high concentrations of a functional material (e.g., 5-100% fabric softening agent or detergent active), fragrance (e.g., 0.5-100%, 0.5-40%, and 0.5-15%), and flavor (e.g., 0.1-100%, 0.1-40%, and 1-20%). They can contain no water to limit the water content as low as less than 30% (e.g., less than 20%, less than 10%, and less than 5%).
  iii. Scent Boosters such as those described in U.S. Pat. Nos. 7,867,968, 7,871,976, 8,333,289, US 2007/0269651 A1, and US2014/0107010 A1.
  iv. Fabric Care Products such as Rinse Conditioners (containing 1-30 weight % of a fabric conditioning active), Fabric Liquid Conditioners (containing 1 to 30 weight % of a fabric conditioning active), Tumble Drier Sheets, Fabric Refreshers, Fabric Refresher Sprays, Ironing Liquids, and Fabric Softener Systems such as those described in U.S. Pat. Nos. 6,335,315, 5,674,832, 5,759,990, 5,877,145, 5,574,179, 5,562,849, 5,545,350, 5,545,340, 5,411,671, 5,403,499, 5,288,417, and 4,767,547 Liquid fabric softeners/fresheners contain at least one fabric softening agent present, preferably at a concentration of 1-30% (e.g., 4-20%, 4-10%, and 8-15%). The ratio between the active material and the fabric softening agent can be 1:500 to 1:2 (e.g., 1:250 to 1:4 and 1:100 to 1:8). As an illustration, when the fabric softening agent is 5% by weight of the fabric softener, the active material is 0.01-2.5%, preferably 0.02-1.25% and more preferably 0.1-0.63%. As another example, when the fabric softening agent is 20% by weight of the fabric softener, the active material is 0.04-10%, preferably 0.08-5% and more preferably 0.4-2.5%. The active material is a fragrance, malodor counteractant or mixture thereof. The liquid fabric softener can have 0.15-15% of capsules (e.g., 0.5-10%, 0.7-5%, and 1-3%). When including capsules at these levels, the neat oil equivalent (NOE) in the softener is 0.05-5% (e.g., 0.15-3.2%, 0.25-2%, and 0.3-1%).

Suitable fabric softening agents include cationic surfactants. Non-limiting examples are quaternary ammonium compounds such as alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. Fabric softening compositions, and components thereof, are generally described in US 2004/0204337 and US 2003/0060390. Suitable softening agents include esterquats such as Rewoquat WE 18 commercially available from Evonik Industries and Stepantex SP-90 commercially available from Stepan Company.

v. Liquid dish detergents such as those described in U.S. Pat. Nos. 6,069,122 and 5,990,065 vi. Automatic Dish Detergents such as those described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562 vii. All-purpose Cleaners including bucket dilutable cleaners and toilet cleaners viii. Bathroom Cleaners ix. Bath Tissue x. Rug Deodorizers xi. Candles xii. Room Deodorizers xiii. Floor Cleaners xiv. Disinfectants xv. Window Cleaners xvi. Garbage bags/trash can liners xvii. Air Fresheners including room deodorizer and car deodorizer, scented candles, sprays, scented oil air freshener, Automatic spray air freshener, and neutralizing gel beads xviii. Moisture absorber xix. Household Devices such as paper towels and disposable Wipes xx. Moth balls/traps/cakes xxi. liquid fragrance compositions or scent drop products each comprising: (i) 3 wt % to 40 wt % (e.g., 5 wt % to 35 wt %, preferably 8 wt % to 30 wt %, and more preferably 10 wt % to 3 wt %) of a fragrance in the form of neat oil or encapsulated in a microcapsule, (ii) 0.5 wt % to 5 wt % (preferably 0.2 wt % to 3 wt %, and more preferably 0.5 wt % to 2.5 wt %) of glyceryl ricinoleate, and (iii) 60 wt % to 95 wt % of water. All amounts are based on the weight of the liquid fragrance composition.

b) Baby Care Products
  i. Diaper Rash Cream/Balm
  ii. Baby Powder c) Baby Care Devices
  i. Diapers
  ii. Bibs
  iii. Wipes d) Oral Care Products. Tooth care products (as an example of preparations according to the invention used for oral care) generally include an abrasive system (abrasive or polishing agent), for example silicic acids, calcium carbonates, calcium phosphates, aluminum oxides and/or hydroxylapatites, surface-active substances, for example sodium lauryl sulfate, sodium lauryl sarcosinate and/or cocamidopropylbetaine, humectants, for example glycerol and/or sorbitol, thickening agents, for example carboxymethyl cellulose, polyethylene glycols, carrageenan and/or Laponite®, sweeteners, for example saccharin, taste correctors for unpleasant taste sensations, taste correctors for further, normally not unpleasant taste sensations, taste-modulating substances (for example inositol phosphate, nucleotides such as guanosine monophosphate, adenosine monophosphate or other substances such as sodium glutamate or 2-phenoxypropionic acid), cooling active ingredients, for example menthol derivatives, (for example L-menthyllactate, L-menthylalkylcarbonates, menthone ketals, menthane carboxylic acid amides), 2,2,2-trialkylacetic acid amides (for example 2,2-diisopropylpropionic acid methyl amide), icilin and icilin derivatives, stabilizers and active ingredients, for example sodium fluoride, sodium monofluorophosphate, tin difluoride, quaternary ammonium fluorides, zinc citrate, zinc sulfate, tin pyrophosphate, tin dichloride, mixtures of various pyrophosphates, triclosan, cetylpyridinium chloride, aluminum lactate, potassium citrate, potassium nitrate, potassium chloride, strontium chloride, hydrogen peroxide, flavorings and/or sodium bicarbonate or taste correctors.

i. Tooth Paste. An exemplary formulation as follows:
    1. calcium phosphate 40-55%
    2. carboxymethyl cellulose 0.8-1.2%
    3. sodium lauryl sulfate 1.5-2.5%
    4. glycerol 20-30%
    5. saccharin 0.1-0.3%
    6, flavor oil 1-2.5%
    7. water q.s. to 100%
      A typical procedure for preparing the formulation includes the steps of (i) mixing by a blender according to the foregoing formulation to provide a toothpaste, and (ii) adding a composition of this invention and blending the resultant mixture till homogeneous.

ii. Tooth Powder
  iii. Oral Rinse
  iv. Tooth Whiteners
  v. Denture Adhesive
e) Health Care Devices
  i. Dental Floss
  ii. Toothbrushes
  iii. Respirators
  iv. Scented/flavored condoms
f) Feminine Hygiene Products such as Tampons, Feminine Napkins and Wipes, and Pantiliners
g) Personal Care Products: Cosmetic or pharmaceutical preparations, e.g., a "water-in-oil" (W/O) type emulsion, an "oil-in-water" (O/W) type emulsion or as multiple emulsions, for example of the water-in-oil-in-water (W/O/W) type, as a PIT emulsion, a Pickering emulsion, a micro-emulsion or nano-emulsion; and emulsions which are particularly preferred are of the "oil-in-water" (O/W) type or water-in-oil-in-water (W/O/W) type. More specifically,
  i. Personal Cleansers (bar soaps, body washes, and shower gels)
  ii. In-shower conditioner
  iii. Sunscreen ant tattoo color protection (sprays, lotions, and sticks)
  iv. Insect repellants
  v. Hand Sanitizer
  vi. Antiinflammatory balms, ointments, and sprays
  vii. Antibacterial ointments and creams
  viii. Sensates
  ix. Deodorants and Antiperspirants including aerosol and pump spray antiperspirant, stick antiperspirant, roll-on antiperspirant, emulsion spray antiperspirant, clear emulsion stick antiperspirant, soft solid antiperspirant, emulsion roll-on antiperspirant, clear emulsion stick antiperspirant, opaque emulsion stick antiperspirant, clear gel antiperspirant, clear stick deodorant, gel deodorant, spray deodorant, roll-on, and cream deodorant
  x. Wax-based Deodorant. An exemplary formulation as follows:
    1. Parafin Wax 10-20%
    2. Hydrocarbon Wax 5-10%
    3. White Petrolatum 10-15%
    4. Acetylated Lanolin Alcohol 2-4%
    5. Diisopropyl Adipate 4-8%
    6. Mineral Oil 40-60%
    7. Preservative (as needed)
      The formulation is prepared by (i) mixing the above ingredients, (ii) heating the resultant composition to 75° C. until melted, (iii) with stirring, adding 4% cryogenically ground polymer containing a fragrance while maintaining the temperature 75° C., and (iv) stirring the resulting mixture in order to ensure a uniform suspension while a composition of this invention is added to the formulation.
  xi. Glycol/Soap Type Deodorant. An exemplary formulation as follows:
    1. Propylene Glycol 60-70%
    2. Sodium Stearate 5-10%
    3. Distilled Water 20-30%
    4. 2,4,4-Trichloro-2'-Hydroxy Diphenyl Ether, manufactured by the Ciba-Geigy Chemical Company and a Trademark of the Ciba-Geigy Chemical Company) 0.01-0.5%.

The ingredients are combined and heated to 75° C. with stirring until the sodium stearate has dissolved. The resulting mixture is cooled to 40° C. followed by addition of a composition of this invention.
  xii. Lotion including body lotion, facial lotion, and hand lotion
  xiii. Body powder and foot powder
  xiv. Toiletries
  xv. Body Spray
  xvi. Shave cream and male grooming products
  xvii. Bath Soak
  xviii. Exfoliating Scrub
h) Personal Care Devices
  i. Facial Tissues
  ii. Cleansing wipes
i) Hair Care Products
  i. Shampoos (liquid and dry powder)
  ii. Hair Conditioners (Rinse-out conditioners, leave-in conditioners, and cleansing conditioners)
  iii. Hair Rinses
  iv. Hair Refreshers
  v. Hair perfumes
  vi. Hair straightening products
  vii. Hair styling products, Hair Fixative and styling aids
  viii. Hair combing creams
  ix. Hair wax
  x. Hair foam, hair gel, nonaerosol pump spray
  xi. Hair Bleaches, Dyes and Colorants
  xii. Perming agents
  xiii. Hair wipes
j) Beauty Care
  i. Fine Fragrance-Alcoholic. Compositions and methods for incorporating fragrance capsules into alcoholic fine fragrances are described in U.S. Pat. No. 4,428,869. Alcoholic fine fragrances may contain the following:
    1. Ethanol (1-99%),
    2. Water (0-99%),
    3. A suspending aide including but not limited to: hydroxypropyl cellulose, ethyl cellulose, silica, microcrystalline cellulose, carrageenan, propylene glycol alginate, methyl cellulose, sodium carboxymethyl cellulose or xanthan gum (0.1%),
    4. Optionally an emulsifier or an emollient may be included including but not limited to those listed above.
  ii. Solid Perfume
  iii. Lipstick/lip balm
  iv. Make-up cleanser
  v. Skin care cosmetic such as foundation, pack, sunscreen, skin lotion, milky lotion, skin cream, emollients, and skin whitening
  vi. Make-up cosmetic including manicure, mascara, eyeliner, eye shadow, liquid foundation, powder foundation, lipstick and cheek rouge
k) Consumer goods packaging such as fragranced cartons, and fragranced plastic bottles/boxes
l) Pet care products
  i. Cat litter
  ii. Flea and tick treatment products
  iii. Pet grooming products
  iv. Pet shampoos
  v. Pet toys, treats, and chewables
  vi. Pet training pads
  vii. Pet carriers and crates m) Confectionaries confectionery, preferably selected from the group consisting of chocolate, chocolate bar products, other products in bar form, fruit gums, hard and soft caramels and chewing gum
   i. Gum
      1. Gum base (natural latex chicle gum, most current chewing gum bases also presently include elastomers, such as polyvinylacetate (PVA), polyethylene, (low or medium molecular weight) polyisobutene (PIB), polybutadiene, isobutene-isoprene copolymers (butyl rubber), polyvinylethylether (PVE), polyvinylbutyether, copolymers of vinyl esters and vinyl ethers, styrene-butadiene copolymers (styrene-butadiene rubber, SBR), vinyl elastomers, for example based on vinylacetate/vinyllaurate, vinylacetate/vinylstearate or ethylene/vinylacetate, as well as mixtures of the mentioned elastomers, as described for example in EP 0 242 325, U.S. Pat. Nos. 4,518,615, 5,093,136, 5,266,336, 5,601,858 or U.S. Pat. No. 6,986,709) 20-25%
      2. Powdered sugar 45-50%
      3. glucose 15-17%
      4. starch syrup 10-13%
      5. plasticizer 0.1%
      6. flavor 0.8-1.2%
         The components described above were kneaded by a kneader according to the foregoing formulation to provide a chewing gum. Encapsulated Flavor or sensate is then added and blended till homogeneous.
   ii. Breath Fresheners
   iii. Orally Dissolvable Strips
   iv. Chewable Candy
   v. Hard Candy
n) Baked products, preferably selected from the group consisting of bread, dry biscuits, cakes and other cookies;
o) snack foods, preferably selected from the group consisting of baked or fried potato chips or potato dough products, bread dough products and corn or peanut-based extrudates:
   i. Potato, tortilla, vegetable or multigrain chips
   ii. Popcorn
   iii. Pretzels
   iv. Extruded stacks
p) Cereal Products preferably selected from the group consisting of breakfast cereals, muesli bars and pre-cooked finished rice products
q) Alcoholic and non-alcoholic beverages, preferably selected from the group consisting of coffee, tea, wine, beverages containing wine, beer, beverages containing beer, liqueurs, schnapps, brandies, sodas containing fruit, isotonic beverages, soft drinks, nectars, fruit and vegetable juices and fruit or vegetable preparations; instant beverages, preferably selected from the group consisting of instant cocoa beverages, instant tea beverages and instant coffee beverages
   i. Ready to drink liquid drinks
   ii. Liquid Drink Concentrates
   iii. Powder Drinks
   iv. Coffee: Instant Cappuccino
      1. Sugar 30-40%
      2. Milk Powder 24-35%
      3. Soluble Coffee 20-25%
      4. Lactose 1-15%
      5. Food Grade Emulsifier 1-3%
      6. Encapsulated Volatile Flavor 0.01-0.5%
   v. Tea
   vi. Alcoholic
r) Spice blends and consumer prepared foods
   i. Powder gravy, sauce mixes
   ii. Condiments
   iii. Fermented Products
s) Ready to heat foods: ready meals and soups, preferably selected from the group consisting of powdered soups, instant soups, and precooked soups
   i. Soups
   ii. Sauces
   iii. Stews
   iv. Frozen entrees
t) Dairy Products milk products, preferably selected from the group consisting of milk beverages, ice milk, yogurt, kefir, cream cheese, soft cheese, hard cheese, powdered milk, whey, butter, buttermilk and partially or fully hydrolyzed milk protein-containing products and flavored milk beverages
   i. Yoghurt
   ii. Ice cream
   iii. Bean Curd
   iv. Cheese
u) Soya protein or other soybean fractions, preferably selected from the group consisting of soya milk and products produced therefrom, soya lecithin-containing preparations, fermented products such as tofu or tempeh or products produced therefrom and soy sauces
v) Meat products, preferably selected from the group consisting of ham, fresh or raw sausage preparations, and seasoned or marinated fresh or salt meat products
w) Eggs or egg products, preferably selected from the group consisting of dried egg, egg white and egg yolk
x) Oil-based products or emulsions thereof, preferably selected from the group consisting of mayonnaise, remoulade, dressings and seasoning preparations
y) fruit preparations, preferably selected from the group consisting of jams, sorbets, fruit sauces and fruit fillings: vegetable preparations, preferably selected from the group consisting of ketchup, sauces, dried vegetables, deep-frozen vegetables, precooked vegetables, vegetables in vinegar and preserved vegetables
z) Flavored pet foods.

The above-listed applications are all well known in the art. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid laundry detergents include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Liquid dish detergents are described in U.S. Pat. Nos. 6,069,122 and 5,990,065. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681. Automatic Dish Detergents are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562.

All parts, percentages and proportions refer to herein and in the claims are by weight unless otherwise indicated.

The values and dimensions disclosed herein are not to be understood as being strictly limited to the exact numerical values recited. Instead, unless otherwise specified, each such value is intended to mean both the recited value and a functionally equivalent range surrounding that value. For Example, a value disclosed as "50%" is intended to mean "about 50%."

The terms "include," "includes," and "including," are meant to be non-limiting.

The terms "capsule" and "microcapsule" herein are used interchangeably.

The terms "polyfunctional isocyanate," "multifunctional isocyanate," and "polyisocyanate" are used interchangeably and refer to a compound having two or more isocyanate (—NCO) groups.

The terms "polyfunctional amine," "multifunctional amine," and "polyamine" are used interchangeably and refer to a compound containing one, two, or more primary or secondary amine groups. These terms also refers to a compound containing one or more primary/secondary amine groups and one or more hydroxyl groups (—OH).

The terms "polyfunctional alcohol," "multifunctional alcohol," "poly alcohol," and "polyol" are used interchangeably and refer to a compound having two or more hydroxyl groups.

The term "curing" as used in polymer chemistry and process engineering refers to a toughening or hardening process of a polymer by cross-linking of polymer chains, brought about by heat, chemical additives, or light radiation.

The invention is described in greater detail by the following non-limiting examples. Without further elaboration, it is believed that one skilled in the art can, based on the description herein, utilize the present invention to its fullest extent. All publications cited herein are incorporated by reference in their entirety.

Example 1

An HEC microcapsule of this invention, i.e., HEC-1, was prepared as follows.

An oil phase was first prepared by mixing 20 grams (g) of a model fragrance and 2 g of caprylic/capric triglyceride (a core solvent, commercially available under the trade name of NEOBEE® oil M-5, Stepan, Chicago, IL). In a separate beaker, an aqueous solution was obtained by mixing an aqueous solution (60 g) containing 10% HEC (commercially available under the trade name of Natrosol™ 250 LR, Ashland Specialty Ingredients, Wilmington, DE), an aqueous solution (5 g) of a 10% sodium salt of polystyrene sulfonate (a capsule formation aid, commercially available under the trade name of Flexan® II, AkzoNobel Surface Chemistry, Ossining, NY), an aqueous solution (10 g) of 1% carboxymethyl cellulose (a capsule formation aid, commercially available under Walocel® CRT50000, Dow Chemical Company, Midland, MI), an aqueous solution (0.2 g) of 20% DABCO crystalline (a catalyst, 1,4-Diazabicyclo[2.2.2]octane, Evonik, Essen, Germany), and a water dispersible aliphatic polyisocyanate (1 g) (a polyisocyanate based on hexamethylene diisocyanate (HDI) commercially available under Bayhydur® 305, Bayer, Leverkusen, Germany). The oil phase was then emulsified into the aqueous phase to form an oil-in-water emulsion under shearing (ULTRA TURRAX™. T25 Basic, IKA WERKE) at 9500 rpm for two minutes.

After the oil-in-water emulsion was stirred at 25° C. for 0.5 hours, 2 g of 25% aqueous glutaraldehyde solution (Sigma-Aldrich, St. Louis, MO) and 30 g of 10% tannic acid aqueous solution (Sigma-Aldrich, St. Louis, MO) were added under constant mixing. After the temperature was raised 55° C., the resultant capsule slurry was stirred for one hour, and then two hours at 75° C. The encapsulation efficiency is 99.9%.

Example 2

Microcapsule HEC-2 of this invention was prepared following the procedure described in Example 1 except that a different water dispersible aliphatic polyisocyanate (a HDI biuret commercially available under the trade name of Desmodur® N100A, Bayer, Leverkusen, Germany) was added in the oil phase instead of Bayhydur® 305 in the aqueous phase. The encapsulation efficiency is 99.9%.

Example 3

Microcapsule HEC-3 of this invention was prepared following the procedure described in Example 2 except that trimethylol propane-adduct of xylylene diisocyanate (commercially available under Takenate™ D100EA, Mitsui Chemicals Inc., Japan) was added to the oil phase instead of Desmodur® N100A that was added to the aqueous phase. The encapsulation efficiency is 99.9%.

Example 4

Microcapsule HEC-4 of this invention was prepared following the procedure described in Example 1 except that the aqueous phase contained a 10% HEC aqueous solution (45 g) and a 10% hydroxyporpyl cellulose aqueous solution (15 g) (Dow Chemical Company, Midland, MI), instead of a HEC solution only. The encapsulation efficiency is 99.9%.

Example 5

An HEC microcapsule of this invention, i.e., HEC-5, was prepared as follows.

An oil phase was first prepared by mixing 20 grams (g) of a model fragrance and 2 g of caprylic/capric triglyceride (NEOBEE® oil M-5). In a separate beaker, an aqueous solution was obtained by mixing an aqueous solution (60 g) of 10% HEC (Natrosol™ 250 LR), an aqueous solution (5 g) of 10% sodium polystyrene sulfonate (Flexan® II), an aqueous solution (10 g) of 1% carboxymethyl cellulose (Walocel® CRT50000), an aqueous solution (0.2 g) of 20% DABCO crystalline, and a water dispersible aliphatic polyisocyanate (1 g) (Bayhydur®) 305). The oil phase was then emulsified into the aqueous phase to form an oil-in-water emulsion under shearing at 9600 rpm for two minutes.

After the oil-in-water emulsion was stirred at 25° C. for 0.5 hours, 2 g of 25% aqueous glutaraldehyde solution and 30 g of 10% tannic acid aqueous solution were added under constant mixing. After the temperature was raised to 55° C., the resultant capsule slurry was stirred for one hour, and then two hours at 75° C. Then pH was adjusted to 7.5 using 25% NaOH solution. A 20% lysine solution (7.5 g) (Sigma-Aldrich, St. Louis, MO) was added. The mixture was stirred for additional two hours at 75° C. The encapsulation efficiency is 99.9%.

Example 6

Microcapsule HEC-6 of this invention was prepared following the procedure described in Example 5 except that 0.67 g 30% branched polyethyleneimine (BASF, Ludwigshafen, Germany) was added instead of lysine.

Example 7

Microcapsule HEC-7 of this invention was prepared following the procedure described in Example 5 except that 0.5 g 40% hexamethylenediamine (Invista, Wichita, KS) was added instead of lysine.

Example 8

Microcapsule HEC-8 of this invention was prepared following the procedure described in Example 5 except that 10 g of a 2% pectin aqueous solution (CP Kelco, Atlanta, GA) was added instead of lysine.

Example 9

An HEC microcapsule of this invention, i.e., HEC-9, was prepared as follows.

An oil phase was first prepared by mixing 14.6 grams (g) of a model fragrance and 1.4 g of caprylic/capric triglyceride (NEOBEE® oil M-5). In a separate beaker, an aqueous solution was obtained by mixing an aqueous solution (43.8 g) containing 10% HEC (Natrosol™ 250 LR), an aqueous solution (3.6 g) of 10% sodium polystyrene sulfonate (Flexan® II), an aqueous solution (7.3 g) of 1% carboxymethyl cellulose (Walocel® CRT50000), an aqueous solution (0.12 g) of 20% DABCO crystalline, and a water dispersible aliphatic polyisocyanate (0.58 g) (Bayhydur® 305). The oil phase was then emulsified into the aqueous phase to form an oil-in-water emulsion under shearing at 9600 rpm for two minutes.

After the oil-in-water emulsion was stirred at 25° C. for 0.5 hours, 1.5 g of 25% aqueous glutaraldehyde solution and 21.9 g of a 10% tannic acid aqueous solution were added under constant mixing. After the temperature was raised 55° C., the resultant capsule slurry was stirred for one hour, and the two hours at 75° C. Then pH was adjusted to 7 using 25% NaOH solution. The mixture was stirred for two hours at 80° C. The encapsulation efficiency is 99.9%.

Example 10

Microcapsule HEC-10 of this invention was prepared following the procedure described in Example 9 except that the water dispersible aliphatic polyisocyanate (0.58 g) (Bayhydur® 305, Bayer, Leverkusen, Germany) was added after emulsion was formed, instead of in the aqueous phase before making the emulsion.

Example 11

Microcapsule HEC-11 of this invention was prepared following the procedure described in Example 9 except that the mixture was stirred for two hours at 85° C. after pH was adjust to 7, instead of two hours at 80° C.

Example 12

Microcapsule HEC-12 of this invention was prepared following the procedure described in Example 9 except that the mixture was stirred for one hour at 90° C. after pH was adjust to 7, instead of two hours at 80° C.

Example 13

An HEC microcapsule of this invention, i.e., HEC-13, was prepared as follows. An oil phase was first prepared by mixing 20 g of a model fragrance and 2 g of caprylic/capric triglyceride (NEOBEE® oil M-5). In a separate beaker, an aqueous solution was obtained by mixing an aqueous solution (60 g) containing 10% HEC (Natrosol™ 250 LR), an aqueous solution (5 g) of a 10% sodium salt of polystyrene sulfonate (Flexan® II), an aqueous solution (10 g) of 1% carboxymethyl cellulose (Walocel® CRT50000), an aqueous solution (0.2 g) of 20% DABCO crystalline (a catalyst), and a water dispersible aliphatic polyisocyanate (1 g) (Bayhydur® 305). The oil phase was then emulsified into the aqueous phase to form an oil-in-water emulsion under shearing at 9500 rpm for two minutes.

After the oil-in-water emulsion was stirred at 25° C. for 0.5 hours, the temperature was raised 55° C. The resultant capsule slurry was stirred for 1 hour at 55° C., and then 2 hours at 75° C.

Example 14

An HEC microcapsule of this invention, i.e., HEC-14, was prepared as follows.

An oil phase was first prepared by mixing 20 g of a model fragrance and 2 g of caprylic/capric triglyceride (NEOBEE® oil M-5). In a separate beaker, an aqueous solution was obtained by mixing an aqueous solution (60 g) containing 10% HEC, an aq. solution (5 g) of a 10% sodium salt of polystyrene sulfonate, an aqueous solution (10 g) of 1% carboxymethyl cellulose, and 30 g of 10% tannic acid aqueous solution. The oil phase was then emulsified into the aqueous phase to form an oil-in-water emulsion under shearing at 9500 rpm for two minutes.

After the oil-in-water emulsion was stirred at 25° C. for 0.5 hours, the temperature was raised 55° C. The resultant capsule slurry was stirred for 1 hour at 55° C., and then 2 hours at 75° C.

Example 15

An HEC microcapsule of this invention, i.e., HEC-15, was prepared as follows.

An oil phase was first prepared by mixing 20 g of a model fragrance and 2 g of caprylic/capric triglyceride. In a separate beaker, an aqueous solution was obtained by mixing an aqueous solution (60 g) containing 10% HEC, an aqueous solution (5 g) of a 10% sodium salt of polystyrene sulfonate, an aqueous solution (10 g) of 1% carboxymethyl cellulose, and 2 g of 25% aqueous glutaraldehyde solution. The oil phase was then emulsified into the aqueous phase to form an oil-in-water emulsion under shearing at 9500 rpm for two minutes.

After the oil-in-water emulsion was stirred at 25° C. for 0.5 hours, the temperature was raised 55° C. The resultant capsule slurry was stirred for 1 hour at 55° C., and then 2 hours at 75° C.

Example 16

An HEC microcapsule of this invention, i.e., HEC-16, was prepared as follows.

An oil phase was first prepared by mixing 20 g of a model fragrance and 2 g of caprylic/capric triglyceride. In a separate beaker, an aqueous phase was obtained by mixing an aqueous solution (60 g) of 10% HEC, an aqueous solution (5 g) of a 10% sodium salt of polystyrene sulfonate, an aqueous solution (10 g) of 1% CMC, 2 g of 25% aqueous glutaraldehyde solution and 30 g of 10% tannic acid aqueous solution. The oil phase was then emulsified into the aqueous phase to form an oil-in-water emulsion under shearing at 9500 rpm for two minutes.

After the oil-in-water emulsion was stirred at 25° C. for 0.5 hours, the temperature was raised 55° C. The resultant capsule slurry was stirred for 1 hour at 55° C., and then 2 hours at 75° C.

Example 17

An HEC microcapsule of this invention, i.e., HEC-17, was prepared as follows.

An oil phase was first prepared by mixing 20 g of a model fragrance and 2 g of caprylic/capric triglyceride. In a separate beaker, an aqueous solution was obtained by mixing an aqueous solution (60 g) of 10% HEC, an aqueous solution (5 g) of a 10% sodium salt of polystyrene sulfonate, an aqueous solution (10 g) of 1% carboxymethyl cellulose, an aqueous solution (0.2 g) of 20% DABCO, and a water dispersible aliphatic polyisocyanate (1 g) (Bayhydur® 305). The oil phase was then emulsified into the aqueous phase to form an oil-in-water emulsion under shearing at 9500 rpm for two minutes.

After the oil-in-water emulsion was stirred at 25° C. for 0.5 hours, 30 g of 10% tannic acid aqueous solution were added under constant mixing. After the temperature was raised 55° C., the resultant capsule slurry was stirred for 1 hour, and then 2 hours at 75° C. HEC-17 has a free oil as low as 0.1% and an encapsulation efficiency as high as 99.9%.

HEC-17 was added to an unfragranced fabric conditioner base. A representative base contains a quat surfactant (active) 1-20%, a stabilizer <1%, a pH buffer <1%, a salt <1%, a preservative <0.1%, and an antifoam <0.1, all by weight of the base.

HEC-17 showed a high stability in the fabric conditioner for a prolonged period of time at an elevated temperature.

Example 18

An HEC microcapsule of this invention, i.e., HEC-18, was prepared following the procedure described in Example 1 except that 2 g of polyisocyanate Bayhydur® 305 was used.

Example 19

An HEC microcapsule of this invention, i.e., HEC-19, was prepared following the procedure described in Example 1 except that 1.7 g of polyisocyanate Bayhydur® 305 was used.

Example 20

An HEC microcapsule of this invention, i.e., HEC-20, was prepared following the procedure described in Example 1 except that 1.3 g of polyisocyanate Bayhydur® 305 was used.

Example 21

An HEC microcapsule of this invention, i.e., HEC-21, was prepared following the procedure described in Example 1 except that 0.7 g of polyisocyanate Bayhydur® 305 was used.

Example 22

An HEC microcapsule of this invention, i.e., HEC-22, was prepared following the procedure described in Example 1 except that 0.3 g of polyisocyanate Bayhydur® 305 was used.

Table 1 below showed the formula of HEC-1, and HEC-18 to HEC-22. The table also included free oil wt % in each microcapsule composition.

TABLE 1

HEC-1 and HEC-18 to HEC-22

| Capsule | Ratio of HEC to polyisocyanate | Bayhydur, wt % | Free Oil |
|---|---|---|---|
| HEC-18 | 2.9 | 1.2 | 4.3% |
| HEC-19 | 3.5 | 1 | 2.5% |
| HEC-20 | 4.4 | 0.8 | 1.4% |
| HEC-1 | 5.8 | 0.6 | <0.1% |
| HEC-21 | 8.8 | 0.4 | 5% |
| HEC-22 | 17.5 | 0.2 | 10% |

Comparative Example 1: Microcapsule Prepared from Hydroxypropyl Cellulose (HPC)

Comparative Microcapsule HPC-1 was prepared following the procedure described in Example 1 except that HPC (Sigma-Aldrich, St. Louis, MO) is used instead of HEC.

Comparative Example 2: Microcapsule Prepared from Hydroxypropyl Cellulose (HPC)

Comparative Microcapsule HPC-2 was prepared following the procedure described in Example 2 except that HPC is used instead of HEC.

Comparative Example 3: Microcapsule Prepared from Hydroxypropyl Cellulose (HPC)

Comparative microcapsule HPC-3 was prepared following the procedure described in Example 3 except that HPC is used instead of HEC.

Comparative Example 4: Microcapsule Prepared from Carboxymethyl Cellulose (CMC)

Comparative Microcapsule CMC-1 was prepared following the procedure described in Example 1 except that CMC (Sigma-Aldrich, St. Louis, MO) is used instead of HEC.

Comparative Example 5: Microcapsule Prepared from CMC

Comparative Microcapsule CMC-2 was prepared following the procedure described in Example 2 except that CMC is used instead of HEC.

Comparative Example 6: Microcapsule Prepared from CMC

Comparative Microcapsule CMC-3 was prepared following the procedure described in Example 3 except that CMC is used instead of HEC.

Comparative Example 7: Microcapsule Prepared from Methyl Cellulose (MC)

Comparative Microcapsule MC-1 was prepared following the procedure described in Example 1 except that MC (Sigma-Aldrich, St. Louis, MO) is used instead of HEC.

Comparative Example 8: Microcapsule Prepared from MC

Comparative Microcapsule MC-2 was prepared following the procedure described in Example 2 except that MC is used instead of HEC.

Comparative Example 9: Microcapsule Prepared from MC Capsule

Comparative microcapsule MC-3 was prepared following the procedure described in Example 3 except that MC is used instead of HEC.

Performance of Hydroxyethyl Cellulose (HEC) Capsule in EU Fabric Conditioner Base To establish the microcapsule performance, HEC-1 was blended into a model fabric conditioner solution. The fragrance load was 0.6% neat oil equivalent (NOE). The perfumery benefit of the capsules was evaluated by conducting a laundry experiment using accepted experimental protocols using European wash machine. Terry towels were used for the washing experiments and were washed with European fabric conditioners containing fragrance loaded capsules before being evaluated by panel of 12 judges. The fragrance intensity is evaluated after gentle tossing of the towels and rated from a scale ranging from 0 to 35. The pre-gentle tossing refers to the evaluations of the towels by panelists before the folding of the towels. The gentle tossing refers to the folding of the towels twice, followed by the evaluation of the towels by panelists. A numerical value of 4 would suggest the fabric only produce weak intensity while a value of 30 indicates the subject generate a very strong smell.

The towel had a pre-toss fragrance intensity of 6.8, a gentle-toss fragrance intensity of 9, and a post-rub intensity of 11.2.

Microcapsules HC-2 to HEC-12 were also evaluated. Each showed unexpected high fragrance intensity.

HEC-1, the neat fragrance oil, Comparative CMC-1, and Comparative MC-1 each were added to the fabric conditioner base. Towels were treated as shown above and then measured by headspace gas chromatography (GC). Table 2 below shows the readings of the headspace GC for each towel treated with a microcapsule composition that is added to the fabric conditioner. A high reading indicates a high concentration of fragrance released into the.

The results show that HEC-1 of this invention has (i) a pre-rub fragrance concentration 3.5 folds that of CMC-1 and 3.7 folds that of MC-1; and (ii) a post-rub fragrance concentration 13.7 folds that of CMC-1 and 8.8 folds that of MC-1.

TABLE 2

| Microcapsule | Pre-rub Intensity | Post-rub Intensity |
| --- | --- | --- |
| Neat fragrance oil | 12611 | 110791 |
| HEC-1 | 302766 | 1051240 |
| Comparative CMC-1 | 86012 | 76253 |
| Comparative MC-1 | 80920 | 118607 |

Consumer Product Examples

Microcapsule compositions of this invention can be added to various consumer products. Non-limiting examples are shown in Table 3 below.

TABLE 3

| Fabric Softener | Antiperspirant (AP) roll-on product |
| --- | --- |
| Microcapsule Composition, 0.1-2% NOE[2]<br>Quat surfactant (active), 1-20%<br>Stabilizer, <1%<br>pH buffer, <1%<br>Salt, <1 %<br>Preservative, <0.1%<br>Antifoam, <0.1<br>Water, q.s. to 100% | Microcapsule Composition, 0.1-2% NOE<br>Anionic surfactant, 1-3%<br>Aluminum chlorohydrate, 10-20%,<br>Silica, less than 1%<br>Helianthus annuus, 1-2%<br>Water, q.s. to 100% |
| Shampoo | Hair conditioner |
| Microcapsule Composition, 0.1-2% NOE<br>Sodium lauryl ether sulphate, 12%<br>Cocamidopropyl betaine, 1.6%<br>Non-ionic guar, 0.2%<br>Silicone, 2-3%<br>Preservative, 0.5%<br>Water, q.s. to 100% | Microcapsule Composition, 0.1-2% NOE<br>Fatty alcohol, 4%<br>Behentrimonium chloride, 0.7%<br>Terminal amino silicones, 1%<br>Silicone, 2.5%<br>Preservative, 0.5%<br>Water, q.s. to 100% |
| Powder detergent Example 1 | Powder detergent Example 2 |
| Microcapsule Composition, 0.1-2% NOE<br>Sodium Carbonate, 81.9%<br>Ethoxylated $C_{12}$-$C_{15}$ alcohol sulfate salt, 4.3%<br>$C_{12}$-$C_{15}$ alcohol ethoxylate, 2.4%<br>Sodium Sulfate, 1.5%<br>Sodium bicarbonate, 1.3%<br>Sodium polyacrylate, 0.7%<br>Sodium Carboxymethylcellulose, 0.1%<br>Optical Brightener, 0.2% | Microcapsule Composition, 0.1-2% NOE<br>Sodium alkl benzene sulphonate, 7.6%<br>Nonionic surfactant, 9.8%<br>Soap, 1.7%<br>sodium aluminosilicate (zeolite), 27%<br>Sodium Carbonate, 13%<br>Alkaline sodium silicate (1:3.3), 0.5%<br>CP5-polymer ex BASF, 4%<br>Sodium Carboxymethylcellulose (SCMC), 0.6%<br>Water, 11% |

TABLE 3-continued

| | |
|---|---|
| Polyvinyl Alcohol, 0.1%<br>Water, 7.4% | Minors, 1.5%<br>Dry Additives<br>Sodium perborate monohydrate (PBM), 14%<br>Enzyme, 1.1%<br>TAED granules (83%), 7.4%<br>Ethylene diamine tetramethylene phosphonate (EDTMP), 0.4%<br>anti-foam granules, 0.4% |
| Powder detergent Example 3 | Roll on deodorant |
| Microcapsule Composition, 0.1-2% NOE<br>Zeolite, 36.6-45.9%<br>Sodium carbonate, 13.3-16.6%<br>Soap, 0-0.7%<br>Sodium sulphate, 0-2%<br>Sodium Carboxymethylcellulose (SCMC), 0-0.9%<br>Fluorescer, 0-0.7%<br>Sodium alkyl benzene sulphonate, 0-23.3%<br>Primary Alkyl sulphate, 0-23.1%<br>Nonionic 7 EO surfactant, 0-4.1%<br>Nonionic 3 EO surfactant, 0-7%<br>CP5 co-polymer ex BASF, 1-3%<br>Alkaline Sodium silicate, 0-4%<br>Water, 11.5-15.8%<br>Liquid detergent<br>Microcapsule Composition, 0.1-2% NOE<br>A non-soap surfactant (anionic or nonionic) with a range of 15 wt. % to 45 wt. %, preferably 32 wt. % to 35 wt. %<br>Propylene glycol, 0.5-50%, preferably 10-20%<br>One or more soil release polymer (SRP) that can be between 0.01% and 10%, preferably 0.9% and 2.5%,<br>Water, 5-35%, preferably 15-25% | Microcapsule Composition, 0.1-2% NOE<br>Aluminum Chlorohydrate 50% Solution, 30-34%<br>Steareth-20, 1.3-1.9%<br>Steareth-2, 5-5.6%<br>Silica, 0.5-1.1%<br>Preservative, 0.7-1.3% |

[1] All component percentages are shown by weight of the consumer product.
[2] NOE is the neat fragrance oil equivalence which equals to the weight percentage of the fragrance oil in the consumer product.

What is claimed is:

1. A microcapsule composition comprising microcapsules that contain a microcapsule core and a microcapsule wall encapsulating the microcapsule core, wherein the microcapsule core contains an active material and the microcapsule wall contains by weight 35% to 90% of a hydroxyethyl cellulose, 2% to 30% of a polyisocyanate, 1% to 50% of a polyphenol, and 0.5% to 20% of a multi-functional aldehyde, provided that the total amount of the hydroxyethyl cellulose, polyisocyanate, polyphenol, and multi-functional aldehyde is equal to or less than 100%, and wherein the hydroxyethyl cellulose and the polyisocyanate reacts to form polyurethane bond, the hydroxyethyl cellulose reacts with the multi-functional aldehyde to form an acetal or hemi-acetal product, and the polyphenol reacts with the polyisocyanate to form a polyurethane polymer.

2. The microcapsule composition of claim 1, wherein the polyisocyanate is water soluble or oil soluble.

3. The microcapsule composition of claim 1, wherein the multi-functional aldehyde comprises glutaraldehyde, glyoxal, di-aldehyde starch, or malondialdehyde.

4. The microcapsule composition of claim 1, wherein the microcapsule wall further comprises hydroxypropyl cellulose.

5. A consumer product comprising the microcapsule composition of claim 1.

6. A method of preparing the microcapsule composition of claim 1, comprising the steps of:
   (a) preparing an oil-in-water emulsion comprising an active material, a hydroxyethyl cellulose, and a polyisocyanate;
   (b) adding a multi-functional aldehyde and a polyphenol to the oil-in-water emulsion; and
   (c) applying conditions sufficient to induce formation of a microcapsule wall comprising by weight, 35% to 90% of the hydroxyethyl cellulose, 2% to 30% of the polyisocyanate, 0.5% to 20% of the multi-functional aldehyde, and 1% to 50% of the polyphenol, thereby preparing the microcapsule composition;
   wherein the hydroxyethyl cellulose and the polyisocyanate reacts to form polyurethane bond, the hydroxyethyl cellulose reacts with the multi-functional aldehyde to form an acetal or hemi-acetal product, and the polyphenol reacts with the polyisocyanate to form a polyurethane polymer.

7. The microcapsule composition of claim 1, wherein the polyphenol is tannic acid.

8. The microcapsule composition of claim 1, wherein the active material is selected from the group consisting of fragrance, pro-fragrance, flavor, malodor counteractive agent, and combinations thereof.

9. The method of claim 6, wherein the polyphenol is tannic acid.

10. The microcapsule composition of claim 1, wherein the polyisocyanate is an oligomer of hexamethylene diisocyanate, a trimer of hexamethylene diisocyanate, a trimer of isophorone diisocyanate, a biuret of hexamethylene diisocyanate, a polyisocyanurate of toluene diisocyanate, a trimethylol propane-adduct of toluene diisocyanate, a trimethylol propane-adduct of xylylene diisocyanate, or a combination thereof.

11. The microcapsule composition of claim 1, wherein the microcapsule has a size of 0.2 μm to 100 μm in diameter, the microcapsule shell constitutes 10% to 90% by weight of the microcapsule, and the microcapsule core constitutes 90% to 10% by weight of the microcapsule.

12. The method of claim 6, further comprising the step of (d) curing the microcapsule at a temperature of 15° C. to 135° C.

13. The method of claim 6, wherein the polyisocyanate is present in the oil-in-water emulsion at a level of 0.01% to 10% by weight of the microcapsule composition.

14. The method of claim 6, wherein the multi-functional aldehyde is added to the oil-in-water emulsion at a level of 0.1% to 2% by weight of the microcapsule composition.

15. The method of claim 6, wherein the hydroxyethyl cellulose is present in the oil-in-water emulsion at a level of 1% to 10% by weight of the microcapsule composition.

16. The method of claim 6, wherein the polyphenol is added to the oil-in-water emulsion at a level of 0.5% to 5% by weight of the microcapsule composition.

\* \* \* \* \*